United States Patent [19]

Engler

[11] Patent Number: 5,900,258
[45] Date of Patent: May 4, 1999

[54] ANTI-BACTERIAL COMPOSITIONS

[75] Inventor: Phillip V. Engler, Carmel, N.Y.

[73] Assignee: Zeolitics Inc., Fairfax, Calif.

[21] Appl. No.: 08/595,111

[22] Filed: Feb. 1, 1996

[51] Int. Cl.⁶ .................................................. A61K 31/12
[52] U.S. Cl. ........................................................... 424/684
[58] Field of Search ............................................. 424/684

[56] References Cited

U.S. PATENT DOCUMENTS

| | | |
|---|---|---|
| 2,882,243 | 4/1959 | Milton . |
| 3,682,996 | 8/1972 | Kerr . |
| 3,691,099 | 9/1972 | Young . |
| 3,708,573 | 1/1973 | Yoshinaga et al. . |
| 3,798,154 | 3/1974 | Bertolacini et al. . |
| 3,836,676 | 9/1974 | Komakine . |
| 3,935,363 | 1/1976 | Burkholder et al. . |
| 4,052,476 | 10/1977 | Morrison . |
| 4,556,560 | 12/1985 | Buckingham . |
| 4,556,645 | 12/1985 | Coughlin et al. . |
| 4,683,318 | 7/1987 | Deffeyes et al. . |
| 4,744,374 | 5/1988 | Deffeyes et al. . |

FOREIGN PATENT DOCUMENTS

| | | |
|---|---|---|
| 6329 800109 | 1/1980 | European Pat. Off. . |
| 2082026 | 1/1972 | France . |
| 2119117 | 11/1972 | Germany . |
| 2302841 | 8/1973 | Germany . |
| 2414201 | 10/1974 | Germany . |
| 2515165 | 10/1975 | Germany . |
| 2617085 | 10/1976 | Germany . |
| 2626840 | 12/1976 | Germany . |
| 48-099402 | 12/1973 | Japan Kokai . |
| 50-018252 | 2/1975 | Japan Kokai . |
| 50-045080 | 4/1975 | Japan Kokai . |
| 50-102328 | 8/1975 | Japan Kokai . |
| 50-148166 | 11/1975 | Japan Kokai . |
| 51-117924 | 10/1976 | Japan Kokai . |
| 59-144722 | 8/1984 | Japan Kokai . |
| 01161053 | 6/1989 | Japan Kokai . |
| 01252641 | 10/1989 | Japan Kokai . |
| 02164368 | 6/1990 | Japan Kokai . |
| 03002113 | 1/1991 | Japan Kokai . |
| 03133627 | 6/1991 | Japan Kokai . |
| 05031858 | 2/1993 | Japan Kokai . |
| 05115760 | 5/1993 | Japan Kokai . |
| 05125618 | 5/1993 | Japan Kokai . |
| 06166623 | 6/1994 | Japan Kokai . |
| 06198607 | 7/1994 | Japan Kokai . |
| 06299038 | 10/1994 | Japan Kokai . |
| 07033906 | 2/1995 | Japan Kokai . |
| 07053832 | 2/1995 | Japan Kokai . |
| 07109404 | 4/1995 | Japan Kokai . |
| 07156344 | 6/1995 | Japan Kokai . |
| 07157650 | 6/1995 | Japan Kokai . |
| 07179694 | 7/1995 | Japan . |

(List continued on next page.)

OTHER PUBLICATIONS

Abstract: Nonomura et al., "Polyurethane moldings having an antimicrobial surface layer and their manufacture," 126 *Chem. Abst.* 20217 (1997) (see L8, answer 1).

Abstract: Oonishi et al., "Antimicrobial powdered coatings and their manufacture," 125 *Chem. Abst.* 303395 (1997)(see L8, answer 2).

Abstract: Mori et al., "Antimicrobial thermoplastic resin compositions," 125 *Chem. Abst.* 169771 (1997)(see L8, answer 3).

Abstract: Okuzono et al., "Microbicidal resin compositions and discoloration prevention," 124 *Chem. Abst.* 31215 (1997)(see L8, answer 4).

Abstract: Hamazaki et al., "Bactericidal polymer compositions," 123 *Chem. Abst.* 200696 (1997)(see L8, answer 5).

Abstract: Okuzono et al., "Antimicrobial resin compositions with good mechanical properties and heat and hot water resistance," 123 *Chem. Abst.* 171511 (1997)(see L8, answer 6).

Abstract: Motai et al., "Bactericidal styrene polymer compositions with good impact resistance," *Chem. Abst.* 241491 (1997)(see L8, answer 7).

Abstract: Honma et al., "Antibacterial silicone rubber compositions," 125 *Chem. Abst.* 331283 (1997)(see L10, answer 1).

Abstract: Morya et al., "Antimicrobial powdered coatings," 125 *Chem. Abst.* 278761 (1997)(see L10, answer 3).

Abstract: Tanizaki et al., "Membrane module of water purification apparatus for prevention of back contamination," 125 *Chem. Abst.* 256697 (1997)(see L10, answer 4).

(List continued on next page.)

*Primary Examiner*—Zohreh Fay
*Attorney, Agent, or Firm*—Kenyon & Kenyon

[57] ABSTRACT

The present invention provides a method for preventing a microorganism from growing on surfaces such as the skin, walls, floors, countertops, and food preparation surfaces as well as in absorbent materials such as diapers, clothing, bedding, bedpads surgical apparel, surgical masks and the like. This method includes incorporating an effective amount of zeolite onto the surface or into the absorbent material to inhibit such a microorganism from growing.

22 Claims, 9 Drawing Sheets

FOREIGN PATENT DOCUMENTS

| | | | |
|---|---|---|---|
| Kokai 07196869 | 8/1995 | Japan . | |
| Kokai 7252398 | 10/1995 | Japan . | |
| Kokai 07324012 | 12/1995 | Japan . | |
| Kokai 07330505 | 12/1995 | Japan . | |
| Kokai 07330581 | 12/1995 | Japan . | |
| Kokai 08026955 | 1/1996 | Japan . | |
| Kokai 08027306 | 1/1996 | Japan . | |
| Kokai 08073742 | 3/1996 | Japan . | |
| Kokai 08089887 | 4/1996 | Japan . | |
| Kokai 08104864 | 4/1996 | Japan . | |
| Kokai 08143746 | 6/1996 | Japan . | |
| Kokai 08150146 | 6/1996 | Japan . | |
| Kokai 08150164 | 6/1996 | Japan . | |
| Kokai 08150194 | 6/1996 | Japan . | |
| Kokai 08157683 | 6/1996 | Japan . | |
| Kokai 08197067 | 8/1996 | Japan . | |
| Kokai 08199089 | 8/1996 | Japan . | |
| Kokai 08206467 | 8/1996 | Japan . | |
| Kokai 08215679 | 8/1996 | Japan . | |
| Kokai 08217998 | 8/1996 | Japan . | |
| Kokai 08239577 | 9/1996 | Japan . | |
| Kokai 08245301 | 9/1996 | Japan . | |
| 7502151 | 8/1975 | Netherlands . | |
| WO 8303594 | 10/1983 | WIPO . | |
| WO 96 01622 | 1/1996 | WIPO . | |
| WO 96 01628 | 1/1996 | WIPO . | |
| WO 96 20016 | 7/1996 | WIPO . | |

OTHER PUBLICATIONS

Abstract: Tanizaki et al., "Water purification apparatus," 125 *Chem. Abst.* 230122 (1997)(see L10, answer 5).

Abstract: Okada et al., "Antibacterial styrene polymer compositions," 125 *Chem. Abst.* 169691 (1997)(see L10, answer 6).

Abstract: Ookita et al., "Antimicrobial resin seals," 125 *Chem. Abst.* 89322 (1997)(see L10, answer 7).

Abstract: Sugishima et al., "Antimicrobial film formation for hospitals and nursing homes," 125 *Chem. Abst.* 35954 (1997)(see L10, answer 8).

Abstract: Motai et al., "Antimicrobial thermoplastic resin compositions," 124 *Chem. Abst.* 345045 (1997)(see L10, answer 10).

Abstract: Kurihara et al., "The formulation and effects of an antimicrobial material, 'Zeomic,' made from zeolite bonded with metallic silver," 124 *Chem. Abst.* 290939 (1997)(see L10, answer 11).

Abstract: Yamamoto et al., "Antiperspirants containing ammonia– and antimicrobial metal–substituted zeolites," 124 *Chem. Abst.* 241774 (1997)(see L10, answer 12).

Abstract: Takizawa et al., "Chronic toxicity and carcinogenity of antibacterial zeolite "zeomic" to mice and rats by oral administration," 124 *Chem. Abst.* 109480 (1997)(see L10, answer 14).

Abstract: Hamazaki et al., "Antibacterial resin resin compositions giving moldings with good surface appearance," 124 *Chem. Abst.* 89033 (1997)(see L10, answer 15).

Abstract: Motai et al., "Antibacterial laminates with Fron resistance," 123 *Chem. Abst.* 316145 (1997)(see L10, answer 16).

Abstract: Inoe et al., "Poly(phenylene ether) compositions and air fans formed thereof," 123 *Chem. Abst.* 315776 (1997)(see L10, answer 17).

Abstract: Kato et al., "Antimicrobial phenolic resin compositions," 123 *Chem. Abst.* 200758 (1997)(see L10, answer 18).

Abstract: Hirasawa et al., "Public hygiene study of replacement A type–zeolite by Ag, Zn, NH3: Part I—subchronic toxicity test," 123 *Chem. Abst.* 49477 (1997)(see L10, answer 19).

Abstract: Tomizawa et al., "Antibacterial resin moldings containing metal ion–exchanged zeolites," 122 *Chem. Abst.* 292506 (1997)(see L10, answer 20).

Abstract: Niuchi et al., "Manufacture of antibacterial decorative panels," 122 *Chem. Abst.* 33820 (1997)(see L10, answer 21).

Abstract: Oohashi et al., "Topical compositions containing antimicrobial agents and siver compounds," 121 *Chem. Abst.* 141737 (1997)(see L10, answer 22).

Abstract: Hayashida et al., "Hydrophilic porous membranes with lasting antibacterial properties and their manufacture," 120 *Chem. Abst.* 9967 (1997)(see L10, answer 23).

Abstract: Yoshida et al., "Electrically conducting antibacterial odor–absorbing synthetic conjugate fibers" 119 *Chem. Abst.* 227941 (1997)(see L10, answer 24).

Abstract: Suzuki et al., "Manufacture of antibacterial plastic films," 119 *Chem.Abst.* 161984 (1997)(see L10, answer 25).

Abstract: Miyaji et al., "Germicidal laminates," 115 *Chem. Abst.* 2814587 (1997)(see L10, answer 26).

Abstract: Ogawara et al., "Antimicrobial oral compositions containing metals carried on zeolites," 115 *Chem. Abst.* 99026 (1997)(see L10, answer 27).

Abstract: Sakamoto et al., "Disinfecting–deodorizing membranes for treating odorous air," 114 *Chem. Abst.* 87862 (1997)(see L10, answer 28).

Abstract: Kobayashi et al., "Manufacture of expanded polystyrene products with sterilizing power" 112 *Chem. Abst.* 200188 (1997)(see L10, answer 29).

Abstract: Okuyama et al., "Manufacture of antimicrobial soft urethane foams," 112 *Chem. Abst.* 37676 (1997)(see L10, answer 30).

Wilding, C.R., et al., "The effects of radiation on intermediate–level waste forms," *Comm. Eur. Communities*, EUR 13559, p. 25, 1991.

Kupriyanov, V.I., et al., "High–vacuum low–temperature adsorption in elongated layers of adsorbents," *PMTF, Zh, Prikl. Mekh. Tekh. Fiz.*, 90.

Arndt, E., "Chrome tanning with a high degree of chromium absorption," *Kozh.–Obuvn. Prom–st., Henkel K. –G.a.A., Duesseldorf, Fed. Rep. Ger.*, vol. 23(12), pp. 44–46, 1981.

Arndt, E., "Alkaline aluminium silicates as agents in the processing of leather and fur," *J. Soc. Leather Technol. Che.,*, vol. 64(5), pp. 98–100, 1980.

Buckingham, J.S. "Laboratory evaluation of an ion exchange process for removing cesium from Purex acid waste solutions," *Energy Res. Abstr.*, vol. 5 p. 1, 1980, *Abstr. No. 272,* 1979.

Hino, Masao, et al. Infrared studies on water adsorption systems with the use of water–d, *Bull. Chem. Soc.*, Japan, vols. 52(7), pp. 2099–2104, 1979.

Gehrke, J. W., Ion exchanger computer program for Zeolon 900 cation exchanges, *Energy Res. Abstr.*, vol.3 (14), 1978, Abstr. No. 32819, 1977.

Sultanov, A.S. et al., "Production of mesitylene on an AShNTs–3 catalyst," Deposited Doc., Viniti, vol. 1222–1274, p. 4, 1974.

Han, In K., et al. "Studies on the nutritive value of zeolite, 2. Effects of a zeolite rice hull mixture on the performance of growing–finishing swine," *Hanguk Ch'uksan Hakhoe Chi*, vol. 18(3), pp. 225–230, 1976.

Denks, V., et al., "Recombination luminescence and color centers of cathodochromic sodalites," *Zh. Prikl. Spektrosk*, vol. 24(1), pp. 37–43, 1976.

Han, In K., et al., "Studies on the nutritive value of zeolite. 1. Substitution levels of zeolite for wheat bran in the rations of growing–finishing swine," *Hanguk Ch'uksan Hakhoe Chi*, vol. 17(5), pp. 595–599, 1975.

Proskurnin, A.L., et al., "Isomerization of 2–methyl–1–pentene on amorophous and amorphous–crystalline aluminosilicates," *Zh. Fiz. Khim*, vol. 49(7), pp. 1807–1808, 1975.

Raskina, L.S., et al., "Comparative characteristics of cracking catalysts," *Izv. Vyssh. Uchebn. Zaved., Neft Gaz*, vol. 18(4),pp. 59–64, 1975.

Izatt, Reed M., et al., "Recent analytical applications of titration calorimetry," *Anal. Calorimetry*, vol. 3 pp. 237–248, 1974.

Zotkin, Yu. M., et al., "Zeolite group mineral in the bauxite deposit in the Krivoi Rog region," *Izv. Dnepropetr. Gron. Inst.*, vol. 58, pp. 77–80, 1973.

Polak, Feliks, et al., "Deactivation of molecular sieves in a modified small–scale autoclave," *Zesz. Nauk. Uniw. Jagiellon.,Pr. Chem.*, vol. 19, pp. 299–310, 1974.

Kuttykamov, S.R., et al., "Catalytic cracking on zeolite catalysts," *Tr. Inst. Khim. Nefti Prir. Solei, Akad. Nauk Kaz. SSR*, vol. 6, pp. 125–129, 1973.

Fujiwara, Tetsuo, et al., "Zeolite resources in the Pirika area, Hokkaido, Japan," *Chika Shigen Chosajo Hokoku*, vol. 46, pp. 105–115, 1974.

Shevtsova, N.N., et al., "Refining of gasoline from thermal cracking on the AShNTs–3 zeolite–containing catalyst," *Izv. Vyssh. Ucheb. Zaved., Neft Gaz*, vol. 17(3), pp. 54–56, 1974.

Bray, G. R., et al., "Heat transfer analysis of a cesium–137 shpping case," *Proc. Int. Symp. Packag. Transp. Radioactive Mater*, vol. 2, pp. 1043–1051, 1971.

Anderson, Richard G. et al., "Strategy for achieving control of paper mill wet end chemistry," *Pap. Trade J.*, vol. 158–(2), pp. 56–59, 1974.

Kurganov, V.M., et al., "Industrial adoption of the catalytic cracking of heavy raw materials using the zeolite–containing catalyst AShNTs–3," *Neftepererab. Neftekhim*, vol. (4), pp. 1–3, 1973.

Korbukh, I.A., et al., "1–Glycosylindazoles," *Tetrahedron Lett.*, No. 46, pp. 4619–4622, 1973.

Shoji, Sadao, et al., "Clay minerals of paddy soils in the Tohoku district. II. Alluvial paddy soils in the area of Takada town, Fukushima Prefecture," *Nippon Dojo–Hiryogaku Zasshi*, vol. 44(6), pp. 197–203 1973.

Travnikova, L.S., et al., "Zeolites in some soils," *Pochvovedenie*, vol. (3), 106–114, 1973.

Ivanov, I.P., et al., "New experimental data for defining more precisely the zeolite facies limits during metamorphism," *Izv. Akad. Nauk SSSR*, 1967, *Ser. Geol.*, vol. (3), pp. 17–28, 1973.

Mumpton, Frederick A., "First reported occurrence of zeolites in sedimentary rocks of Mexico," *Amer. Mineral.*, vol. 58(3–4), pp. 287–290, 1973.

Piontkovskaya, M.A., et al., "Preparation of an aluminozeolite ion–exchange resin for removing potassium ions from erythrocyte hemolyzates," *Gematol. Pereliv. Krovi*, No. 7, pp. 149–151, 1972.

Kurihara, Yasuo, "The formulation and effects of an antimicrobial material," *Purasuchikkusu Eji*, vol. 42(3), pp. 152–156, 1996.

Takizawa, Yukio, et al., "Chronic toxicity and carcinogenicity of antibacterial zeolite "zeomic" to mice and rats by oral administration," *Nippon Shokuhin Kagaku Gakkaishi*, vol. 2(1), pp. 21–35, 1995.

Hirasawa, Fujiko, et al., "Public hygiene study of replacement A type–zeolite by Ag., Zn, NH3. Part I–subchronic toxicity test," *Nippon Shokuhin Kagaku Gakkaishi*, vol. 1(1), pp. 54–62, 1994.

Chemical Abstracts 125:151246 (1994). Sato.

Chemical Abstracts 124:185636 (1994). Kawai et al.

ANTI-BACTERIAL COMPOSITIONS

FIELD OF THE INVENTION

The present invention relates to novel methods for preventing microbial growth and the breakdown of urea to ammonia in absorbent materials and on surfaces such as, for example, diapers, clothing, bedsheets, bedpads, blankets, filters, filtering aides, wall coverings, countertops, cutting boards, and the like. These methods involve contacting the microorganism with an absorbent material or a surface which contains an effective amount of a zeolite.

BACKGROUND OF THE INVENTION

Bacteria growth can lead to disease, particularly when the species of bacteria is pathogenic. Even when a bacterial species is not normally pathogenic, a person or animal which is immunologically compromised may become infected with that bacterial species. While antibiotics are often used to combat such bacterial infections, bacteria can become resistent to those antibiotics and excessive use of antibiotics is frequently blamed for the occurrence of antibiotic-resistant bacteria. Moreover, many people are allergic to certain types of antibiotics and antibiotic usage can cause gastrointestinal upset or other side effects. For example, more than 75% of infants prescribed Amoxycillin™ or Augmentin™ develop diarrhea, which causes a four-fold increase in the probability of developing a diaper-area dermatology disease. Similarly, agricultural animals are healthier and more productive when bacterial exposure is reduced but antibiotic usage, with its attendant side effects and tendencies to give rise to antibiotic-resistant strains of bacteria, has been the only effective procedure for accomplishing these results. Hence, new methods are needed for preventing exposure of mammals to bacteria and for inhibiting bacterial growth once such exposure has occurred.

For example, methods for reducing bacterial growth in and on materials which are used near or by hospital patients, infants, the elderly and other persons whose immune systems are weakened, would greatly reduce the need for antibiotic usage. Similarly, methods for inhibiting bacterial growth in materials which contact the skin of such persons can prevent dermatological problems. Methods for inhibiting bacterial growth on surfaces used for food preparation would reduce the incidence of food poisoning. Methods of reducing bacterial growth in the litter, bedding and even the soil where domesticated animals are maintained would reduce animal mortality and increase yields of eggs, meat and milk.

Some materials are known to support bacterial growth, for example, the urine and feces captured by a diaper, but no method currently exists for inhibiting such growth. Even though it is initially sterile, bacteria and other microbes frequently begin to grow in urine and, when the skin is exposed to urine for any length of time, dermatological problems can result. Similarly, fecal material is rife with microorganisms that can cause dermatological problems, e.g. by producing proteolytic enzymes and lipases. These dermatological problems can also be created or exacerbated by ammonia formed by the breakdown of urea. The skin and tissues are irritated by ammonia at concentrations of 10,000 ppm; higher exposures produce burns and blistering. Adult tissues and moist membranes are irritated by ammonia gas at concentrations as low as 35 ppm for 15 minutes. See Proctor et al., *Chemical Hazards of the Workplace* (2d ed. 1988); 2B *Patty's Industrial Hygiene and Toxicology* 3045 (1981); Clayton and Clayton, *Safety Standards for Industrial Chemicals* (1981); NIOSH, *Criteria for Recommended Standard Exposure to Ammonia* (1981); *American Conference of Governmental Industrial Hygienists* (1987). Moreover, ammonia gas can be life-threatening to healthy adults at levels of about 1500 parts per million (ppm) over about two hours. The safe industrial limit of exposure to ammonia by adults is 35 to 50 ppm for 15 minutes. Breathing 5000 ppm can be immediately fatal. Bacterial growth exponentially increases the rate of ammonia formation.

Infants and the elderly can be even more sensitive to dermatological problems and to the effects of ammonia. For example, low birth weight infants often have underdeveloped respiratory systems which may be especially vulnerable to the toxic effects of ammonia. Infants and the elderly with any form of pulmonary disfunction such as bronchopulmonary dysplasia, chronic respiratory failure and pulmonary hypertension may succumb to ammonia poisoning more easily than healthy individuals.

For example, a baby urinates about 0.75 ml to 1.0 ml of urine per hour per kilogram of bodyweight. Urine is about 96% water, 2% urea and 2% other materials. The excreted urine passes through a membrane-sleeve of conventional disposable diapers, which are highly effective at absorbing water but not very effective at absorbing ammonia or ammonium ions. Moreover, while water is held tightly, a conventional diaper does not prevent microbial growth. In the presence of such microbes, urea present from excreted urine and feces begins to break down in minutes into ammonia and ammonium, by the following formulae:

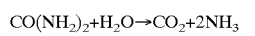

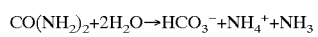

The rate of in vitro ammoniation increases hourly by 5.8%, 6.3%, 8.0% and 9.7% through hours 2 to 5 after voiding. This steeply increasing rate of ammoniation is caused by growing colonies of bacteria and the consequent accumulation of urease which deaminates urea.

The pH of urine at the time of voiding is about 6.0, but, as $NH_4OH$ and $NH_3$ continually form over time the pH rises. At about three hours the pH is about 9.0 and $NH_3$ gas flows continuously. While some microbial growth is retarded by pH 6.0 urine, an increased pH stimulates bacterial growth. Each urination provides fresh urea to start a new cycle of deamination. Ammonia is also formed by breakdown of microbial amino acids. This rising pH provides an increasingly hospitable environment for bacterial and other microbial colonies.

Moreover, even though the growth of microbes is momentarily slowed by a fresh voiding of pH 6.0 urine, such microbes quickly recover, continue growing and decompose more urea and amino acids.

Once ammonia gas is formed, it begins escaping back across a disposable diaper's membrane-sleeve where it contacts the skin and feces, if present. Ammonia elevates the pH of whatever medium it contacts. For example, the alkaline ammonia gas elevates the fecal pH which activates proteolytic enzymes that vigorously metabolize skin, causing irritations, rashes or lesions. Such damage makes the skin more vulnerable, not only to ammonia, but to opportunistic microbes, including fungi such as Candida, and bacteria that normally do not inhabit the skin.

When disposable diapers become saturated with urine, pressure of 0.5 psi will force urine back through the membrane-sleeve where it contacts skin and feces, a phenomenon known as "re-wetting." Frequently, disposable diapers become saturated and the membrane-sleeve bursts open, permitting urine to contact skin and feces. In either case, this urine is aged or ripe and contains deaminating urea, ammonium, ammonium hydroxide, dissolved ammonia, ammonia gas and carbon dioxide, as well as a potentially enormous inoculum of urea-cleaving bacteria. Large numbers of bacteria can be toxic, especially if they enter body cavities or if subdermal areas of the epidermis have been breached. The carbon dioxide is known to be toxic when breathed, and is believed to cause fatal hypercarbia to infants in certain conditions. See Thach, J. PEDIATRICS (June, 1993); Kemp & Thach, PEDIATRIC RES. (July 1994); Kinney et al. SCIENCE (September 1995). A combination of ammonia gas and carbon dioxide is believed to be more toxic than either gas alone.

According to the present invention, zeolites prevent microbial growth thereby inhibiting urea from converting to ammonia and carbon dioxide. Therefore, zeolites have two beneficial effects: inhibition of bacterial growth and inhibition of ammonia and carbon dioxide production.

Zeolites can be chemically synthesized and also occur naturally in volcanic rocks, altered basalts, ores and clay deposits. Zeolites include crystalline, hydrated alkali-aluminum silicates of the general formula:

$$M_{2/n}O\cdot(Al_2O_3)\cdot[y(SiO_2)]\cdot wH_2O$$

wherein M is a cation of valence n, w is the number of water molecules, and y is 2 or more. The cation is mobile and can undergo ion exchange. See U.S. Pat. No. 2,882,243 to Milton.

Zeolites have been used as catalysts, adsorbents and ion exchange media in chemical and hydrocarbon processing procedures. Some forms of crystalline aluminosilicate zeolites are regenerated after use in such procedures, often by acid treatment or thermal treatment at very high temperatures. Resistance to such treatment is related to the presence of a higher proportion of $SiO_2$ relative to $Al_2O_3$ in the aluminosilicate. See U.S. Pat. No. 3,691,099 to Young.

Crystalline, hydrated aluminous tectosilicates of Group I and II elements such as potassium, magnesium and calcium are also formed in nature or may be synthesized in the laboratory. Higher polyvalent ions, such as the rare earths, are readily introduced by cation exchange. Structurally, these tectosilicates form an aluminous silicate "framework" extending as an infinite three-dimensional network of $AlO_4$ and $SiO_4$ tetrahedra linked together by shared oxygen atoms. These aluminous tectosilicates are represented by the empirical unit cell formula:

$$M_{x/n}[(AlO_2)_x(SiO_2)_y]\cdot wH_2O$$

wherein M is a cation of valence n, w is the number of water molecules, x is the number of $AlO_2$ units and y is the number of $SiO_2$ units. The ratio of y/x is usually about 1 to about 10. The sum of x and y is the total number of tetrahedra in the unit cell.

Channels and pores uniformly penetrate the entire volume of the solid zeolite. When water is removed from these zeolites, large internal surface areas become available to absorb liquids or gases. Thus, the external surface area of a zeolite represents only a small portion of its total available surface area. Moreover, the dehydrated zeolite selectively absorb or reject different molecules on the basis of their effective molecular sizes and shapes.

Point electric charges on the surfaces of aluminous zeolite pores absorb highly polar molecules such as water, alcohols and the like. Such hydrophilicity has been exploited to remove water from polar substances which are less readily absorbed by the aluminous zeolite, for example, hydrocarbons processed by the petroleum industry. Gas streams may also be dried with a dehydrated zeolite due to its extremely strong attraction for water. Both naturally-occurring and synthetically-prepared zeolites have been used to remove nitrogenous components from liquid human and animal wastes by ion exchange. See U.S. Pat. No. 3,935,363 to Burholder. Metal catalysts have been introduced into zeolites for converting carbon monoxide to carbon dioxide or for catalyzing the hydrogenation and cracking of petroleum feedstocks. See British Patent No. 2,013,476A. Hydrophobic tectosilicates, developed to resist water absorption, will absorb less polar substances from mixtures containing water. See U.S. Pat. Nos. 4,744,374 and 4,683,318. For example, U.S. Pat. No. 3,682,996 to Kerr disclosed silylation of free hydroxy sites in zeolites by trimethylsilane ($H-Si(CH_3)_3$) and that such silylated zeolites absorbed about 40% less cyclohexane, n-hexane and water than the parent "hydrogen" zeolites of type II. However, Kerr did not report any change in selectivity preference. Similarly, R. M. Barrer and J. -C. Trombe, J. C. S. Faraday I, 74, 1871 (1978), reported some nest silylation to form a tectosilicate of structure V ($R=SiH_3$, x<4) but were largely unsuccessful in replacing lattice aluminum with silicon, reporting that nest hydroxyl groups appeared to be less reactive to silylation than are the hydroxyl groups of the present structure II.

However, there has been no recognition of the present beneficial properties of either hydrophilic or hydrophobic zeolites for preventing microbial growth and for preventing the conversion of urea and amino acids to ammonia. Instead, skin rashes and irritations are frequently treated with salves and ointments. For example, U.S. Pat. No. 4,556,560 to Buckingham provides a lipase-inhibiting agent which is preferably applied with a barrier-like vehicle for treatment of diaper rash and diaper dermatitis. Medicated greases such as Balmex® and A&D Ointment® are also widely available. However, while these products may provide some protection from ammonia burns, they also block oxidation of the injured skin and create an ideal environment for growth of anaerobic bacteria. Therefore, a long-standing need exists for a new solution to dermatological problems such as diaper rash and dermatitis.

SUMMARY OF THE INVENTION

The present invention provides a method for preventing a microorganism from growing in a diaper, clothing, bedding or a bedpad by incorporating an effective amount of zeolite into the diaper, clothing, bedding or bedpad to inhibit the microorganism from growing.

This and other objectives of the present invention are more specifically described in the detailed description of the invention, provided hereinbelow.

BRIEF DESCRIPTIONS OF THE DRAWINGS

FIG. 1 depicts procedures for derivatization of aluminous tectosilicates. Starting materials are depicted by formula I:

$$(\equiv Si-O)_4Al\_M^+ \qquad\qquad I$$

wherein $M^+$ is a metal cation. These starting materials are treated with acid to provide aluminum-associated hydroxyl sites on the tectosilicate of formula II:

$$(\equiv Si-O)_3Al+HO-Si\equiv \qquad\qquad II$$

Exposure to a silylating agent, for example trimethylsilane, provides a silylated, aluminum-containing material of formula III:

(≡Si—O)₃Al⁺(CH₃)₃Si—O—Si≡   III

Alternatively, extended treatment of aluminous tectosilicates with aqueous acid provides tectosilicates with a high proportion of silicon to aluminum. These dealuminated tectosilicates contain tetracoordinated hydroxylated nests of about four ≡Si—OH moieties, as depicted by formula IV. Heating at low temperatures of about 100° C. to 200° C. clears pores and channels in the tectosilicates by removing water of hydration. Treatment with a derivatizing reagent, RX, yields derivatized, dealuminated tectosilicates of formula V:

(≡Si—OR)ₓ   IV wherein R is alkyl, acyl, or silyl substituted with 1–3 halogen, alkoxy alkyl, aryl, aralkyl or cycloalkyl substituents.

FIG. 2 depicts the log reduction of *Staphlococcus aureus* cell titer caused by several dilutions of a 45 mg/ml clinoptilolite derivatized with dichlorodimethylsilane (DCDMS Zeolog). The log reduction is log (initial cell titer/final cell titer), where the initial titer was $9.2 \times 10^9$ colony forming units per ml of culture (cfu/ml). As illustrated, all zeolog dilutions between $10^{-1}$ and $10^{-5}$ reduced the *Staphlococcus aureus* cell titer, but a dilution of $10^{-1}$ almost completely inhibited cell growth (by causing a $3 \times 10^9$ cfu/ml reduction in cell titer).

FIG. 3 depicts the log reduction of *Staphlococcus aureus* cell titer caused by several dilutions of a 45 mg/ml clinoptilolite derivatized with methyltriethoxy groups (PQ99 Zeolog, also known as ZeoLog-MeTE). The log reduction is log (initial cell titer/final cell titer), where the initial titer was $9.2 \times 10^8$ cfu/ml. As illustrated, zeolog dilutions between $10^{-1}$ and $10^{-2}$ reduced the *Staphlococcus aureus* cell titer, but a dilution of $10^{-1}$ caused more cell growth inhibition (about a $2 \times 10^8$ cfu/ml reduction in cell titer).

FIG. 4 depicts the log reduction of *Staphlococcus aureus* cell titer caused by several dilutions of a 45 mg/ml clinoptilolite derivatized with methanol (MeOH Zeolog, also known as ZeoLog Methanol). The log reduction is log (initial cell titer/final cell titer), where the initial titer was $9.6 \times 10^8$ cfu/ml. As illustrated, zeolog dilutions between $10^{-1}$ and $10^{-5}$ completely inhibited *Staphlococcus aureus* cell growth, causing a $6 \times 10^8$ cfu/ml reduction in cell titer.

FIG. 5 depicts the log reduction of *Escherichia coli* cell titer caused by several dilutions of a 45 mg/ml clinoptilolite derivatized with dichlorodimethylsilane (DCDMS Zeolog). The log reduction is log (initial cell titer/final cell titer), where the initial titer was $7.9 \times 10^8$ cfu/ml. As illustrated, zeolog dilutions between $10^{-1}$ and $10^{-2}$ completely inhibited *Escherichia coli* cell growth, the $10^{-3}$ dilution caused a $1 \times 10^7$ cfu/ml reduction in cell titer, and the $10^{-4}$ dilution caused a $1 \times 10^2$ cfu/ml reduction in cell titer.

FIG. 6 depicts the log reduction of *Escherichia coli* cell titer caused by several dilutions of a 45 mg/ml clinoptilolite derivatized with methyltriethoxy groups (MTTXY-Zeolog, also known as ZeoLog-MeTE). The log reduction is log (initial cell titer/final cell titer), where the initial titer was $7.9 \times 10^8$ cfu/ml. As illustrated, zeolog dilutions between $10^{-1}$ and $10^{-2}$ inhibited *Escherichia coli* cell growth, by $9 \times 10^7$ and $9 \times 10^2$ cfu/ml, respectively.

FIG. 7 depicts the log reduction of *Salmonella typhimurium* cell titer caused by several dilutions of a 45 mg/ml clinoptilolite derivatized with dichlorodimethylsilane (DCDMS Zeolog). The log reduction is log (initial cell titer/final cell titer), where the initial titer was $3.6 \times 10^9$ cfu/ml. This type of derivatized zeolite provided little reduction in *Salmonella typhimurium* cell titer.

FIG. 8 depicts the log reduction of *Salmonella typhimurium* cell titer caused by several dilutions of a 45 mg/ml clinoptilolite derivatized with methyltriethoxy groups (MTTXY Zeolog, also known as ZeoLog-MeTE). The log reduction is log (initial cell titer/final cell titer), where the initial titer was $7 \times 10^9$ cfu/ml. As illustrated, zeolog dilutions of $10^{-3}$ and $10^{-4}$ reduced the *Salmonella typhimurium* cell titer by $9 \times 10^{-2}$ and $4 \times 10^5$ cfu/ml, respectively.

FIG. 9 depicts the log reduction of *Salmonella typhimurium* cell titer caused by several dilutions of a 45 mg/ml clinoptilolite derivatized with methanol (MeOH Zeolog, also known as ZeoLog Methanol). The log reduction is log (initial cell titer/final cell titer), where the initial titer was $2.1 \times 10^9$ cfu/ml. As illustrated, $10^{-4}$ and $10^{-5}$ dilutions of a 45 mg/ml suspension of methanol-derivatized zeolite effectively reduced the *Salmonella typhimurium* cell titer by about $2 \times 10^4$ and $4 \times 10^5$ cfu/ml, respectively.

DETAILED DESCRIPTION OF THE INVENTION

Figure 1:
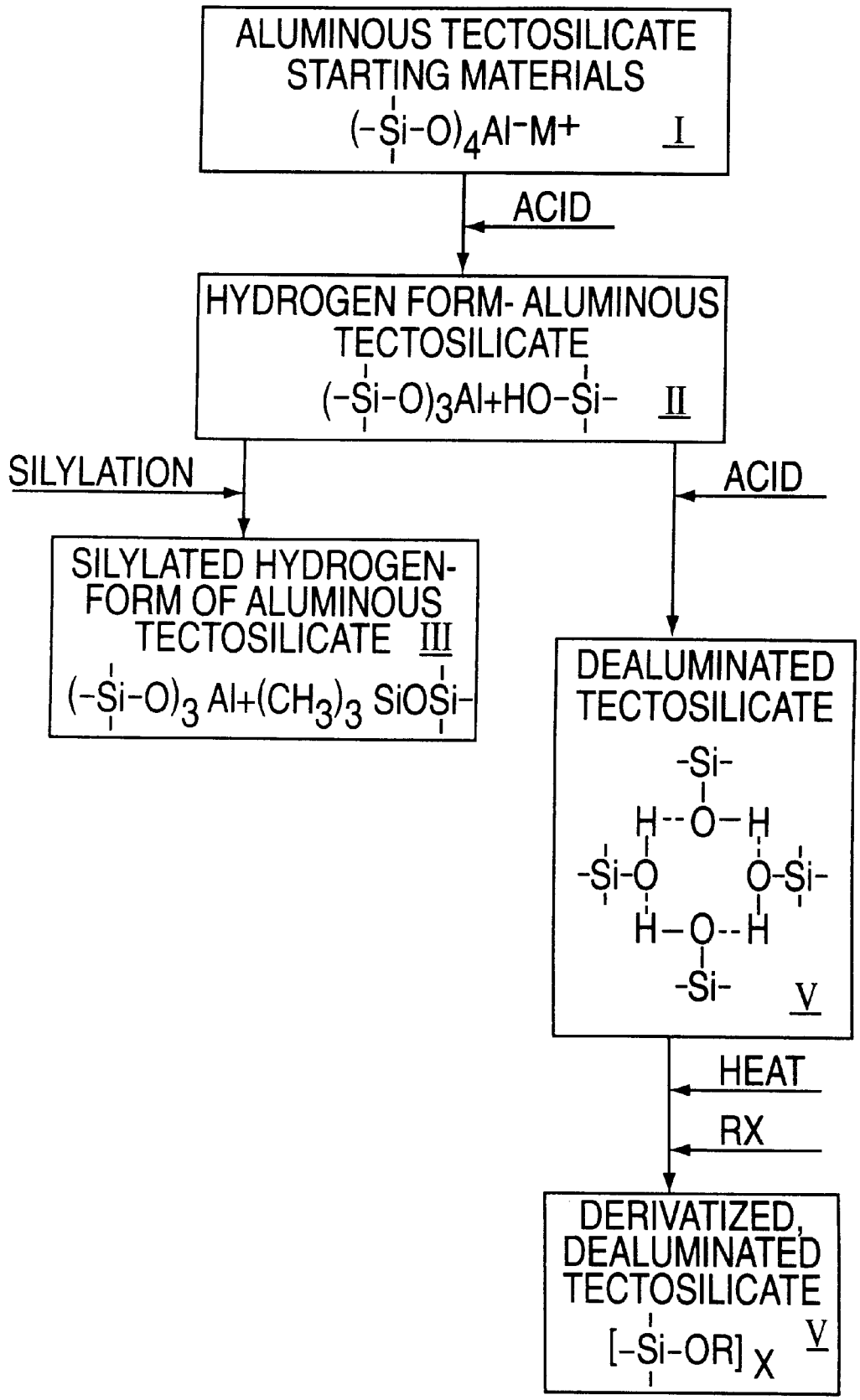
Figure 2:
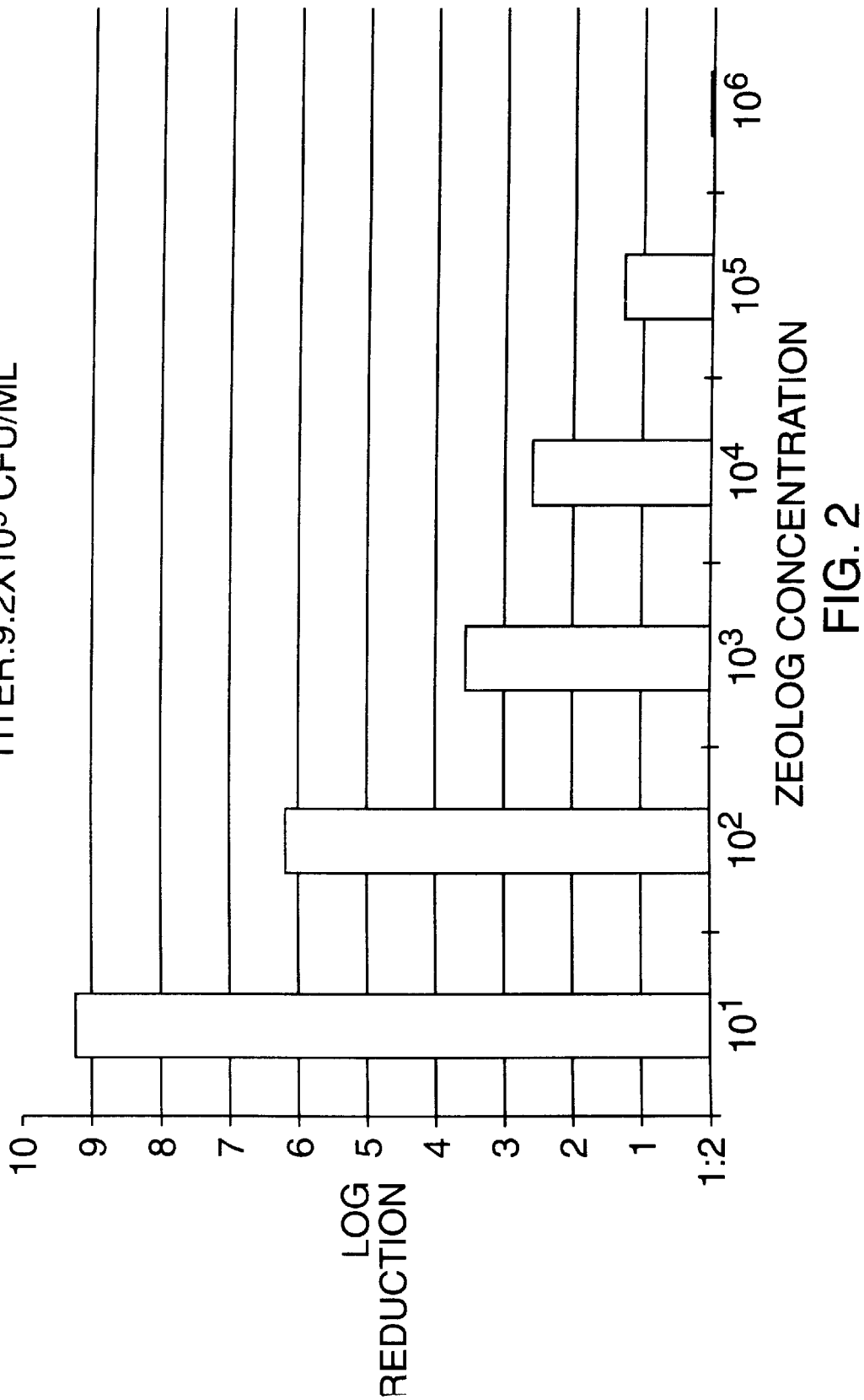
Figure 3:
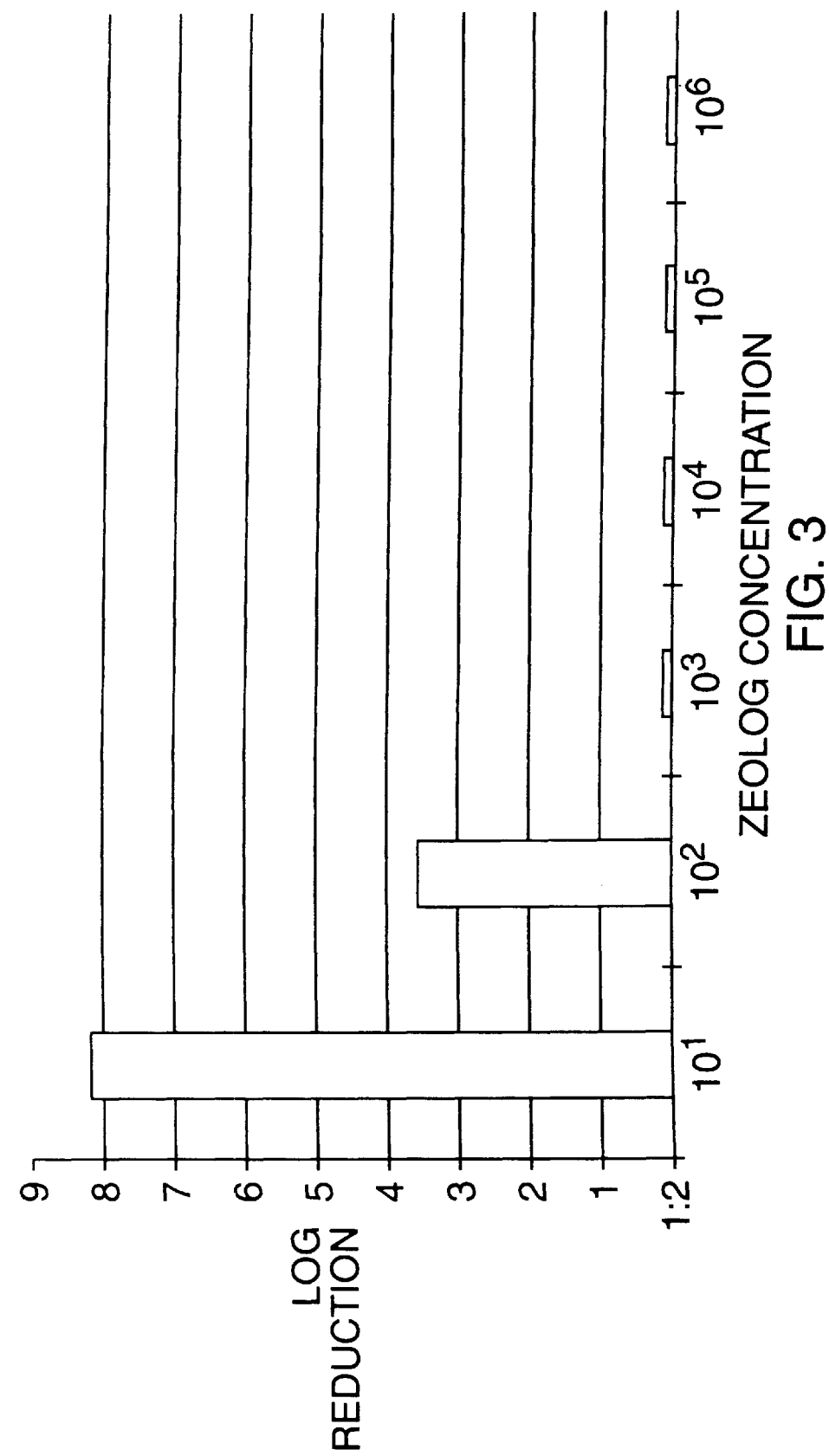

According to the present invention, microbial growth is inhibited by zeolites. Use of zeolites therefore prevents bacterial infections and rashes in mammals, for example, when used in materials that may contact hospital patients, in surfaces used for food preparation, in diapers, in bedding, in bedpads and the like. Prevention of bacterial growth also prevents ammonia formation which can cause or exacerbate skin rashes.

The methods of the present invention prevent microorganisms from growing, for example, on the skin, in diapers, in clothing, in bedding, in bedpads, in wallcoverings, in paint, in surgical apparel, in surgical masks, on countertops, in cutting boards and the like. Such microorganisms grow on these materials particularly when food, urine, feces, perspiration and the like are present.

The present invention contemplates methods of inhibiting growth and urea breakdown by microorganisms commonly found on the skin and in decaying food, urine, perspiration and feces. Growth of bacteria commonly found in hospitals can also be inhibited. Such microorganisms include members of the family Enterobacteriaceae as well as a large number of gram positive microbes. Gram negative Enterobacteriaceae which are included in the present invention are members of the genus Proteus, including *P. mirabilis, P. vulgaris, P. penneri* and *P. myxofaciens*. Other genera contemplated by the present invention include Klebsiella, Providencia, Yersinia, Erwinia, Enterobacter, Salmonella, Serratia, Aerobacter and Escherichia. In addition, related gram negative genera fall within the scope of the invention, including Pseudomonas, Shegella, Vibrio, Aeromonas, and Campylobacter.

The gram positive microorganisms falling within the scope of the invention include the following genera, Streptococcus, Staphylococcus, Lactobacillus, Micrococcus and the Moraxella-Neisseria group.

The present methods are especially effective for preventing growth of *Escherichia coli* and *Staphylococcus aureous*.

Moreover, the present methods are effective for preventing growth of ammonia-producing microorganisms, e.g. those disclosed in J. J. Leyden, Urinary Ammonia and Ammonia-Producing Microorganisms in Infants With and Without Diaper Dermatitis, 113 ARCHIVES OF DERMATOLOGY (December 1977). Such ammonia-producing microorganisms include the aerobic diptheroids found on human skin, Corynebacterium and *Brevibacterium ammoniagenes*.

The present methods are practiced on both humans and animals. In a preferred embodiment, the present methods are used for hospital patients, for infants, for the elderly, for farm animals and for food preparation. In an especially preferred embodiment, the present methods are used for treating infants and the elderly who have skin irritations, rashes or lesions.

While not wishing to be limited thereby, the methods of the present invention may compromise cell wall processes including basic transport processes. For example, zeolites may capture or neutralize electrons and inhibit electron transport through key enzymes of the electron transport chain such as cytochrome oxidase.

Both naturally-occurring and synthetic zeolites are used in the methods of the present invention. Both aluminated and de-aluminated zeolites are contemplated by the present invention, but, in one embodiment, dealuminated zeolites are preferred. Dealuminated zeolites have interior acid sites provided by protons which are left when the aluminum is removed. These interior acid sites react with, and hold cations such as ammonia. Because the interior acid sites are inside the zeolite materials, these acid sites do not touch the skin. In another embodiment, preferred zeolites are derivatized with substituents that are weaker point electric sources than hydroxy. Such dealuminated and derivatized zeolites not only bind ammonia in the presence of water but also inhibit microbial growth.

Synthetic zeolites for use in the present methods include zeolites derivatized with dichlorodimethyl silane, ZeoLog-MeTE, ZeoPhob™, ZeoLog™, ZeoLogCN-METHANOL™, Zeolite A (see U.S. Pat. No. 2,882,243); Zeolite B (see U.S. Pat. No. 3,008,803); Zeolite D (see Canada Patent No. 611,981); Zeolite E (see Canada Patent No. 636,931; Zeolite F (see U.S. Pat. No. 2,995,358); Zeolite H (see U.S. Pat. No. 3,010,789); Zeolite J (see U.S. Pat. No. 3,011,869); Zeolite KG (see U.S. Pat. No. 3,056,654); Zeolite L (see Belgium Patent No. 575,117); Zeolite M (see U.S. Pat. No. 2,995,423); Zeolite O (see U.S. Pat. No. 3,140,252); Zeolite Q (see U.S. Pat. No. 2,991,151); Zeolite R (see U.S. Pat. No. 3,030,181); Zeolite S (see U.S. Pat. No. 3,054,657); Zeolite T (see U.S. Pat. No. 2,950,952); Zeolite W (see U.S. Pat. No. 3,012,853); Zeolite X (see U.S. Pat. No. 2,882,244); Zeolite Y (see U.S. Pat. No. 3,130,007); and Zeolite Z (see Canada Patent No. 614,995).

Naturally-occurring aluminosilicate zeolites which are used in the present methods include analcite, brewsterite, chabazite, clinoptilolite, dachiardite, datolite, erionite, faujasite, ferrierite, flakite, gmelinite, harmotone, heulandite, leucite, levynite, mesolite, mordenite, natrolite, nepheline, noselite, paulingite, phillipsite, scolecite, stilbite, and yugawaralite. Naturally-occurring zeolites are preferred. A preferred naturally-occurring zeolite is clinoptilolite.

The hydrophobic zeolites of the present invention are prepared by removing a substantial proportion of the aluminum from the lattice sites of a tectosilicate, dehydrating the resulting aluminum-deficient tectosilicate and substituting lattice silyl hydroxyl groups with organic moieties which are weaker point electric sources than aluminum. As used herein the term "weaker point electric source" is a moiety which has a lower overall charge, or a charge which is distributed over a larger molecular volume, than the charge, for example, of an aluminum site in an aluminous tectosilicate, or a hydroxyl site formed as a result of aluminum removal. Preferred embodiments have organic moieties which are weaker point electric sources than hydroxy, such as acyl, alkyl, silyl and the like.

Preferably, the lattice silyl hydroxyl groups have a tetracoordinate "nest" configuration. Preferred silyl groups are those of the general formula $Si(R')_n X_p$ wherein n is 0 to 3, p is 3–n, R' is selected from the group consisting of aryl, alkyl, acyl, aralkyl, cycloalkyl and mixtures thereof and X is halogen or an alkoxy group. The preferred acyl, alkoxy and alkyl groups are lower acyl, alkoxy and alkyl radicals such as $C_1$–$C_4$ alkyl, alkoxy or acyl groups, both branched and straight chain. Preferably, n is 1–2 and X is chloro.

The tectosilicates derivatized in this manner are first dealuminated so as to produce the requisite reactive sites in the silicaceous lattice. Preferably, dealumination is accomplished by treatment with aqueous mineral acid. The dealuminated tectosilicate is then dehydrated to expose reactive lattice silyl hydroxyl groups. Tectosilicates generally possess some hydroxyl (OH) groups, but the number of hydroxyls is not sufficient to allow derivatization to the extent necessary to impart a useful degree of hydrophobicity. Accordingly, the substrate tectosilicates is first treated to increase the number of lattice hydroxyl groups, and then is dehydrated to make the hydroxyl groups available for subsequent chemical derivatization. Derivatization is by known procedures, e.g. those provided in U.S. Pat. Nos. 4,683,318 and 4,744,374 to Deffeyes, the disclosures of which are incorporated herein by reference.

A general reaction scheme for derivatizing tectosilicate zeolites is depicted in FIG. 1. Exposure of tectosilicates to aqueous acids replaces the metal cation (M+) of tectosilicates with a hydronium ion. As depicted in FIG. 1, a Si—O—Al bond of starting material I readily protonates and dissociates to provide aluminum-associated hydroxyl sites within the lattice as shown by structure II. These type II sites are silylated by known procedures, for example as disclosed in U.S. Pat. No. 3,682,996 to Kerr or U.S. Pat. No. 4,683,318 to Deffeyes. In one embodiment, such silylation is by exposure to trimethylsilane (H—Si(CH$_3$)$_3$) to form silylated, aluminum-containing material of structure III.

Aluminous tectosilicates having a silicon to aluminum ratio (Si:Al) of greater than about 5 are almost totally dealuminated without loss of lattice integrity. See R. M. Barrer and M. B. Makki, 42 Can. J. Chem. 1481 (1964). This is accomplished by extended treatment of aluminous tectosilicates with aqueous acid. Dealumination yields tectosilicates having tetracoordinated hydroxylated nests containing about 4 associated ≡Si—OH moieties, as depicted in structure IV. These aluminum-free sites are termed "exoaluminum sites".

Activated tectosilicate materials both of structure II and IV exhibit reduced hydrophilicity because of the absolute reduction of lattice charge from aluminum removal, but still absorb water via hydrogen bonding to hydrogen atoms associated with the remaining aluminum atoms and/or to the free silyl hydroxyl (SiOH) groups. Heating aluminum-containing or dealuminated tectosilicates to relatively low temperatures, i.e., to about 100°–200° C., preferably in the presence of a vacuum, clears pores and channels for absorption by removing water of hydration from the pores. However, exposure of dealuminated tectosilicates to higher temperatures, i.e., to about 400°–500° C., causes either partial or total destruction of the hydroxyl nests, via dehydroxylation and formation of new Si—O—Si bonds. Dealuminized mordenites having Si:Al ratios of greater than 80 will not absorb water vapor at a pressure of one or 12 mm of mercury. See N. Y. Chen in J. Phys. Chem. 80, 60 (1976).

The aluminous tectosilicates utilized as starting materials for preparing derivatized tectosilicates can include crystalline, amorphous and mixed crystalline amorphous tectosilicates of natural or synthetic origin or mixtures thereof. The water insoluble crystalline tectosilicates useful in the present invention are those that possess interstitial channels of a narrowest diameter of about 3–13 Å. Hereinafter this diameter will be referred to as pore size.

A preferred pore size for the unmodified substrate materials which is useful in this invention is about 3–10 Å, most preferably 3–8 Å. The pore size of any given tectosilicate must be large enough to admit derivatization materials such as silanes, alcohols and the like, yet small enough to prohibit entry of unwanted liquid or gas stream components, i.e., aromatics, ketones, heterocyclic compounds and the like. Tectosilicates possessing pore sizes with the range of about 4–13 Å readily admit small gaseous elements and compounds such as water (kinetic diameter [σ] 2.65 Å), carbon monoxide (σ=3.76 Å), carbon dioxide (σ-3.30 Å) and ammonia (σ=2.60 Å).

The most useful aluminous tectosilicate starting materials preferably possess a lattice silicon to aluminum ratio of greater than about 5:1. Tectosilicates having a silicon to aluminum ratio of less than about five tend to lose their structural integrity upon dealumination.

An especially preferred class of aluminous tectosilicate starting materials is the naturally-occurring clinoptilolites. These minerals typically have the unit cell structure of the formula:

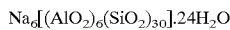
$$Na_6[(AlO_2)_6(SiO_2)_{30}]\cdot 24H_2O$$

wherein the sodium ion content (Na+) is partially replaced by calcium, potassium and/or magnesium, etc. The silicon:aluminum ratio in preferred varieties is greater than 5 and most preferably greater than about 8. The pore size is in the range of about 3.0–6.0 Å. Clinoptilolite is stable in air to about 700° C. and maintains its structural integrity upon dealumination.

Other naturally-occurring aluminous tectosilicates that are useful as starting materials are the mordenites, which typically exhibit the unit cell composition:

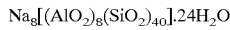
$$Na_8[(AlO_2)_8(SiO_2)_{40}]\cdot 24H_2O$$

wherein calcium and potassium cations can replace a part of the sodium cations. The pore size is in the range of about 3.5–4.5 Å. The silicon to aluminum ratio is generally greater than 5 but can be greater than 10. Other aluminous tectosilicates such as ferrierite or erionite also provide useful starting materials.

Although naturally-occurring aluminous tectosilicates are acceptable starting materials, the synthetic analogs of the natural tectosilicates and their derivatives are of equivalent utility in the present method. For example, synthetic mordenite (Zeolon®), available from the Norton Company, is an acceptable starting material for providing derivatized zeolites. Also, other synthetic, porous tectosilicates which have no equivalent in nature could serve as acceptable starting materials.

The formation of the hydrophobic materials of the present invention normally proceeds in three steps: (1) dealumination, (2) dehydration and (3) derivatization with an appropriate alkylating, acylating or silylating agent.

The dealumination of aluminous tectosilicates with acid is well known in the art. For example, R. M. Barrer & M. B. Makki (42 Canadian J. Chem. 1481 (1964)) reported the complete dealumination of clinoptilolite by refluxing samples in aqueous hydrochloric acid of varying concentration. In the present method, a strong acid treatment is preferred, involving exposing pulverized, sieved aluminous tectosilicate to refluxing, i.e. boiling 2–10N aqueous mineral acid for about 1–3 hours. Strong acids such as hydrochloric acid, sulfuric acid, nitric acid or phosphoric acid are preferably used. The more preferred acid is hydrochloric acid, at concentrations of about 3N to about 7N.

In some cases, dealumination is accomplished by a mild acid treatment involving the percolation of aqueous acid through a column of crushed aluminous tectosilicate under ambient conditions. Preferably, the tectosilicate starting material is dealuminated to achieve a Si:Al ratio of greater than about 25, but preferably the ratio exceeds 100, e.g. about 150–300. Under the most preferred conditions essentially no lattice aluminum is retained, as measured by X-ray fluorescence.

The dealuminated, air-dried tectosilicate materials are then heated in order to remove most of the pore water of hydration and to expose the remaining lattice hydroxyl groups to derivatization. The heating is carried out at any temperature sufficient to effect substantial dehydration without causing significant lattice rearrangement and subsequent loss of reactive sites. Typically, the dealuminated materials are heated to about 100°–200° C. for about 10–40 hours, preferably under reduced pressure. Derivatization after high temperature treatment at about 500°–600° C., does not cause a further increase in hydrophobicity for tectosilicates that had been subjected to the acid treatment at ambient temperatures, although substantial hydrophobicity is exhibited by the samples relative to the starting materials.

Following thermal dehydration at lower temperatures, e.g., about 100°–200° C., the majority of lattice silyl-hydroxyl groups which are present in tetracoordinated nests of the unit structure IV, as depicted in FIG. 1. The dealuminated, dehydrated materials are cooled and then exposed to derivatizing reagents that functionalize these internal lattice silyl-hydroxyl groups. After exposure of the aluminum-free sites ("exoaluminum sites") to the derivatizing reagent, the nest sites contain from about 1–4 [Si—OR] units wherein R is alkyl, acyl, or silyl, substituted with 1–3 halogen, alkoxy, alkoxy alkyl, aryl, aralkyl or cycloalkyl substituents wherein the alkyl, alkoxy or acyl groups, either directly attached to the lattice silyloxy or bound to the silicon atom of the R group, preferably are $C_1$–$C_4$ alkyl, alkoxy or acyl groups.

Reagents (RX) useful to replace the hydrogen atom of the nest silyl-hydroxyl groups with the substituent R include a wide range of the reagents known in organic chemistry to be useful to alkylate, acylate or silylate hydroxyl groups. Such agents are generally disclosed by I. T. Harrison et al. in *Compendium of Organic Synthetic Methods*, Wiley-Interscience, N.Y. (1971) at pages 124–131, the disclosure of which is incorporated by reference herein.

Preferred reagents include the lower-$C_1$–$C_4$-alkanols, $C_1$–$C_4$ alkyl or $C_1$–$C_4$ alkyl halides such as methanol, ethanol and the like or methyl chloride, methyliodide, ethyl chloride, butyl bromide and the like. Lower-$C_1$–$C_4$-alkanols have been found to be especially effective as derivatizing agents when thermally reacted with the tectosilicates under pressure either neat or in the presence of catalysts. Other useful alkylating reagents include the $C_1$–$C_4$-diazo-alkanes.

In one embodiment, nest hydroxyl groups are acylated by exposure to ketenes such as ketene itself or to alkyl or dialkyl ketenes such as dimethylketene. Reaction of a silyl-hydroxyl group with ketene yields an SiOR moiety wherein R is acetyl, aralkyl and mixtures thereof; and X is a halogen atom, i.e., Cl, F, I, Br or mixtures thereof, or a (lower) alkoxy group.

Di-, tri- or tetra-functional silylation reagents also react with two to four ≡Si—OH groups in a single nest to functionally replace the missing aluminum atom with the bridging unit $SiR'_q$, wherein q is 0–2, thus bridging the aluminum-deficient site with 1–2 silicon atoms. This reaction occurs via the elimination of 2–4 HX groups and the formation of O—Si—O bridges. For example, when dimethyldichlorosilane is reacted with lattice silyl hydroxyl groups (≡Si—OH), structural units such as ≡SiOSi(CH$_3$)$_2$Cl or ≡SiOSi(CH$_3$)$_2$OSi are introduced into the nests. The methyl groups are replaced with any of the groups represented by R' and Cl is replaced by another halogen atom or by an alkoxy group.

Typical monofunctional silylating reagents which introduce Si(R')$_3$ units include trimethylchlorosilane, trimethylflurosilane, dimethyliso-propyl-chloro-silane and the like. Preferred dysfunctional silylating agents include the dihalodialkylsilanes, e.g., dichlorodimethylsilane and the dialkoxy(dialkyl) silanes, e.g., diethoxy-dimethylsilane. Tri- and tetra-functional silanes are also employed to derivatize the tectosilicates of the present invention, such as silicon tetrafluoride, tetrachlorosilane, and trifluoromethylsilane.

Reaction of the dealuminated, dehydrated tectosilicates with the silylation reagent is carried out by contacting the materials with the reagent in the liquid or gas phase. Preferably, an excess of silylation reagent in a suitable solvent is slurried with the tectosilicate. Heating and/or added catalysts are employed if necessary, depending on the reactivity of the tectosilicate and the silane.

Gaseous hexamethyldisilazane is reacted with lattice hydroxyl groups to introduce trimethylsilyl groups into the nests, following the procedure of Fenimore et al., *Anal. Chem.*, 48, 2289 (1976), the disclosure of which is incorporated herein by reference.

These procedures readily afford hydrophobic microporous, crystalline silaceous materials which exhibit a greatly reduced affinity for water while maintaining high affinities for less polar molecules such as ammonia. The hydrophobicity or reduction in hydrophilicity of a tectosilicate is quantitated in terms of its absorption of water per unit of tectosilicate under a given set of exposure conditions (retention volume). That any observed reduction in water retention is due to hydrophobicity as opposed to a general reduction in retention is established by measuring the retention of a similarly-sized molecule of comparable or lesser polarity, such as ammonia, nitrogen, methane or carbon dioxide.

Microporous crystalline silaceous materials with reduced affinity for water vapor are useful in the methods of the present invention. The tectosilicates are acid treated and activated for derivatization by heating, but not actually derivatized. Reductions in water retention are observed from about 10% to about 50%, and preferably about 15% to about 45%, of the absorption capacity observed prior to the derivatization step. Water retention is measured in terms of ml H$_2$O/g material at standard temperature and pressure. When ammonia vapor retention is used as a reference, the absorption of water vapor into the derivatized material is no more than about 20% to about 80% that of ammonia. Often, less that 20% water is absorbed relative to ammonia.

In contrast, both ammonia and water are irreversibly absorbed on heat dehydrated or hydrated tectosilicate samples which have not been treated with acid or derivatized and exhibit retention volumes of greater than 200 ml of vapor per column-gram of aluminous tectosilicate under the gas-solid chromatography conditions used to measure retention volumes Therefore, the derivatized tectosilicates effectively absorb ammonia from wet human or animal excreta.

The present methods are practiced by incorporation of naturally-occurring zeolites and zeolites prepared as described hereinabove in diapers, bedpads, blankets, sheets, undergarments, outer clothing and the like. Zeolites are incorporated into vapor-permeable compartments and moisture-permeable compartments, or distributed throughout the textile matrix.

Bedpads and disposable diapers typically consist of an absorbent core of natural or synthetic fibers, a permeable top or inner sheet and a liquid-impervious back or outer sheet. While an effective amount of zeolite can be incorporated into any of these layers, the zeolite is preferably incorporated into the absorbent core of the diaper or bedpad.

An effective amount of zeolite is incorporated into, or solution-coated onto, sheets, blankets, wipes, premoistened towelettes, disposable diaper top sheets, plastic pants linings, cloth diapers, diaper pails and the like. Such methods of dispersing particulate solids onto and into fibrous substrates are known in the art.

The amount of zeolite used varies from about 1% to 50%, preferably about 15% to 25% of the weight of the material. The amount used may depend on the particular use, for example, whether the material is intended for day or night use and whether the material is intended for use by an infant or an elderly person.

The methods of the present invention are also practiced with animals. For example, zeolites of the invention can be incorporated into animal litter, either alone or in combination with other absorbent materials. Typical animal litter consists of absorbent inorganic or organic materials such as attapulgite, vermiculite and calcium montmorillonite (i.e., clay), agglomerated wood dust, wood chips, dehydrated grasses, straw, or alfalfa, fly ash and the like. The present zeolites are added in an effective amount, e.g. about 5–95%, preferably about 20% to 30% or more (based on total litter weight) to inhibit microbial growth and ammonia formation in the litter without substantially reducing the litter's absorbent characteristics. For convenience, such litter preparations are aggregated into pellets.

The invention is further illustrated by reference to the following non-limiting examples.

EXAMPLE 1

The following six procedures were used to modify the properties of clinoptilolite (Hector, Calif., NL Industries).

Procedure A$_1$ —Mild Acid Wash

The tectosilicate, i.e., clinoptilolite, was crushed in a jaw crusher, then pulverized in a Braun Pulverizer. The pulverized material was passed through a 50–100 mesh RoTap® sieve agitator and used to fill 2-inch diameter, 3-foot long Pyrex® tube two-thirds full. The powdered material was held in place with a glass wool plug. Forty liters of hydrochloric acid (6N) were poured through the packed column at a rate of about 9 ml/min. at 27° C. The acid-treated material was washed by flushing with three column volumes of distilled water, then air-dried. Clinoptilolite (Hector, Calif.) treated in this manner was light green and exhibits a Si:Al ratio of approximately 30.

Procedure A$_2$ —Strong Acid Wash

The light green material 9225 g) isolated from procedure A$_1$ was placed in a 4.0 liter round bottomed flask and 2.01 of 6N HCl was added. The slurry was heated at reflux for 2.0 hours. A white mineral was recovered by vacuum filtration and washed repeatedly with deionized water. The Si:Al ratio of clinoptilolite treated in this manner was about 212.

Procedure $H_1$ —Mild Heat Treatment

About 10 g of pulverized tectosilicate (clinoptilolite) was placed in a 250 ml beaker and heated to 150° C. for 20 hours in a vacuum drying oven at less than 10 mm Hg. After vacuum heating, the material was stored at 150° C. at ambient pressure.

Procedure $H_2$ —High Heat Treatment

About 10 g of pulverized tectosilicate (clinoptilolite) was placed in a quartz 250 ml beaker and heated at 550° C. for 14 hours at ambient pressure, then transferred to a 150° C. oven for storage at ambient pressure.

Procedure $D_1$ —Silylation

Pyridine was allowed to stand over potassium hydroxide pellets for 24 hours, then distilled from barium oxide and stored over 4 Å molecular sieves. Toluene was refluxed over sodium metal for three days, then distilled and stored over Linde type 4 Å molecular sieves. A reagent mixture of 20% pyridine, 15% dichlorodimethylsilane and 65% toluene was prepared and stored over the molecular sieves.

A 250 ml round bottomed flask equipped with magnetic stirring, a reflux condenser and argon inlet was flushed with dry argon and charged with 10 g of pulverized tectosilicate followed by addition of 100 ml of the reagent mixture described hereinabove. The resultant slurry was refluxed for 20 hours. After reaction, the acid-treated tectosilicate material was isolated by filtration and washed with dry toluene and methanol. The material was refluxed for at least two hours in methanol, recovered by filtration and stored under ambient conditions.

Procedure $D_2$ —Methylation

About 5.0 g of pulverized material was placed in a steel bomb with about 50 ml of methanol. The bomb was sealed and heated to 220° C. for 4–12 hours. The bomb was cooled to 25° C. and the material recovered by filtration.

EXAMPLE 2

Determination of Gas Retention Volumes

The treated, pulverized tectosilicate was vacuum-packed into a silylated glass column (0.125 inch inner diameter, 0.25 inch outer diameter) and held in by plugs of silylated glass wool. The column was inserted into the oven of a gas chromatograph. The injector port was maintained at 200° C., the detector oven at 250° C. and the column maintained at an initial conditioning temperature of 45°–50° C. for 10–30 minutes. The detector filament current was held at 150 mA and the carrier gas (He) inlet pressure was 60 psi. Gas injections (75–125 $\mu$) were made at 407 psi above ambient pressure and liquid injections were of 1–2 $\mu$l. Water and ammonia retention volumes were measured at a column temperature of 200° C. Under these conditions, ammonia was irreversibly absorbed. Results were expressed as K (ml of gas absorbed/g of absorbent at STP).

The properties of a number of modified Hector, Calif. clinoptilolites prepared by various combinations of the procedures described above are summarized in Table I. In all cases the procedures were performed or omitted in the order indicated. The silicon:aluminum ratios were determined by energy-dispersive X-ray spectrometry (Tracor spectrace model 440, Tracor-Northern 2000 Analyzer) with data reduction accomplished using the program Super ML, Tracor X-Ray, Inc.

TABLE I

| Sample | Treatment[1] | K($H_2O$)[2] | Si/Al | Total Carbon Analysis (%)[5] |
|---|---|---|---|---|
| 1 | none | >200 | 10.00 | 0.28 |
| 2 | $A_2H_1D_2$ | 21 | High[3] | 0.69 |
| 3 | $A_2H_1D_1$ | 26 | High[3] | 0.62 |
| 4 | $A_2H_1D_0$ | 36 | 211.67 | 0.12 |
| 5 | $A_1H_1D_2$ | 58 | 39.58 | 0.52 |
| 6 | $A_1H_2D_0$ | 59 | 6.93[4] | 0.30 |
| 7 | $A_1H_2D_1$ | 64 | 32.66 | 0.63 |
| 8 | $A_1H_1D_1$ | 79 | 33.00 | 2.37 |
| 9 | $A_1H_1D_0$ | 93 | 34.43 | 0.38 |
| 10 | $A_1H_0D_2$ | 129 | 33.56 | 0.29 |
| 11 | $A_1H_0D_0$ | >200 | 10.82[4] | N.T. |
| 12 | $A_1H_0D_1$ | >250 | 39.01 | 2.90 |
| 13 | $A_1H_2D_2$ | >570 | 6.8[4] | 0.36 |

[1]Treatments $A_1$, $A_2$, $H_1$, $H_2$, $D_1$, and $D_2$ are described in Example 1. $D_0$ treatment indicates no derivatization; $H_0$ treatment indicates no heat treatment.
[2]ml/g at STP: K($NH_3$) was >200 in all cases.
[3]Lattice Al not detected in these materials.
[4]Anomalous results probably due to operator error.
[5]Galbraith Laboratories, Inc., Knoxville, Tenn.

Table I illustrates that mild or strong acid washes followed by high or low temperature heating significantly increases the hydrophobicity of the tectosilicate even without a further derivatization step. The effect was most pronounced in the case of samples washed with strong acid, then heated at 150° C. ($A_2H_1D_0$, Sample 4). However, samples 3 and 2 demonstrate that a further significant increase in hydrophobicity can be attained by silylation or methylation, respectively, of this material. The total percent carbon was also increased in these samples by over 400% in each case. Likewise, an increase in hydrophobicity was observed in the case of the silylation (Sample 8) or methylation (Sample 5) of the material of Sample 9, which had been subjected to the mild acid wash and then to 150° C. heating. The greater affinity for water observed for these samples, as opposed to samples 3 and 2, was thought to reflect the presence of more reactive sites, i.e., silyl nests, in the latter two materials, which had been exposed to stronger dealumination conditions.

Mild heat treatment before derivatization retains lattice structure and minimizes collapse of hydroxyl or other reactive sites. Sample 6 was made by mild acid treatment but high heat treatment. Derivation of sample 6 by silylation and methylation formed samples 7 and 13, respectively. However, samples 7 and 13 exhibit little or no increase in hydrophobicity relative to sample 6, indicating derivatization was ineffective. A comparison of samples 8 and 7, with 9 and 6 indicates that, for otherwise equivalently-prepared samples, a high heat treatment ($H_2$) results in a significantly lower carbon incorporation when either methylation or silylation was attempted. While not wishing to be limited, poor derivatization may be due to the collapse of hydroxyl nests or other reactive sites by high heat treatment.

Silylation of material which had been acid washed but not dehydrated by heat (sample 12) failed to increase the hydrophobicity of the material of sample 11, possibly due to the blockage of reactive sites by water of hydration. Methylation of the same material caused a moderate increase in hydrophobicity (sample 10). Thus, the activated nests following acid treatment were best produced and preserved by mild heat treatment.

The hydrophobic derivatized materials of samples 3 and 2 possessed no detectable lattice aluminum by X-ray fluoroscopy, a negative result also expected and observed in the case of silicalite® (Union Carbide). This provides confirmation that the strong acid wash conditions were effective to remove lattice aluminum and to produce reactive hydroxyl-containing nests that were available for derivatization. Although removal of lattice aluminum is, by itself, adequate to significantly increase the hydrophobicity of the clinoptilolite, and, in fact, was the major contributor to the hydrophobic properties involved, it was apparent from samples 8, 3, 5 and 2 that the hydrophobic properties were optimized, for this set of treatment variables, by further silylation or methylation. Significant hydrophobic affects are generally observed in both derivatized and nonderivatized materials when the Si:Al ratio exceeds about 25.

The hydrophobic materials of samples 8, 3, 5 and 2 would be expected to absorb significant amounts of ammonia from wet human or animal excreta, and to do so more effectively than any material employed heretofore, such as nonderivatized tectosilicates, phyllosilicate clays, silica gel and the like.

EXAMPLE 3

Inhibition of Microbial Growth by Derivatized Zeolites Materials

Three dried cultures of E. coli (ATCC 25922), S. aureus (ATCC 6538) and s. typhimurium (ATCC 14028) were rehydrated with four ml of Difco's Brain Heart Infusion broth (BHI) and incubated at 37° C. for twenty hours. Standard plates containing Difco's Tryptic Soy Agar (TSA) were prepared for spread plating. A single tube of 4.5 ml nutrient broth with no zeolite was prepared as a positive control. Two sets of six tubes containing 4.5 ml nutrient broth were prepared for quantifying bacteria treated with each of zeolite DCDMS (dichlorodimethylsilane derivatized clinoptilolite), ZeoLog-MeTE (methyltriethoxy derivatized clinoptilolite) and ZeoLog-METH (methanol derivatized clinoptilolite). Six of these tubes were to be used for testing how bacteria responded to zeolite treatment; the other six tubes were to be used for pH measurement on days two and three. Six rows of ten tubes containing 4.5 ml 0.1% Beef Peptone Water (BPW) were also prepared for quantifying of bacteria treated with zeolite by serial dilution. A similar series of ten tubes was also prepared for titer of the positive control which would receive no zeolite.

Methods

The twenty hour cultures were collected from the incubator and a growth initiation titer (GIT) was performed by plating 0.1 ml of $10^{-6}$ to $10^{-10}$ dilutions on TSA.

To determine the effect of zeolite on survival of a bacterial species, 4.5 ml of a 45 mg zeolite/Ml nutrient broth solution was placed in a tube and 0.5 ml of a $10^{-4}$ dilution of bacterial culture was added. This tube was designated the original $10^{-1}$ dilution tube. This original $10^{-1}$ solution was serially diluted by sequential placement of 0.5 ml into tubes containing 4.5 ml of a 45 mg zeolite/Ml nutrient broth to a final dilution of $10^{-6}$. The 0.5 ml removed from the original ($10^{-1}$) tube was replaced with 0.5 ml of 45 mg zeolite/Ml nutrient broth so that each tube in the series would have the same volume. A similar series of bacterial dilutions were made in nutrient broth containing no zeolite to create a positive control. The set of six zeolite-nutrient broth tubes to be used for measuring the effect of zeolite on pH received no bacteria. All tubes were placed in a 37° C. shaking incubator for twenty hours.

The next day, the tubes and the GIT plates were taken out of the incubator. Ten fold dilutions were made of each zeolite treatment culture and 0.1 ml of these dilutions were spread plated on TSA plates. The plates were incubated for twenty hours and the number of colonies were counted. The pH of the uninoculated tubes was recorded.

Results

Figure 4:
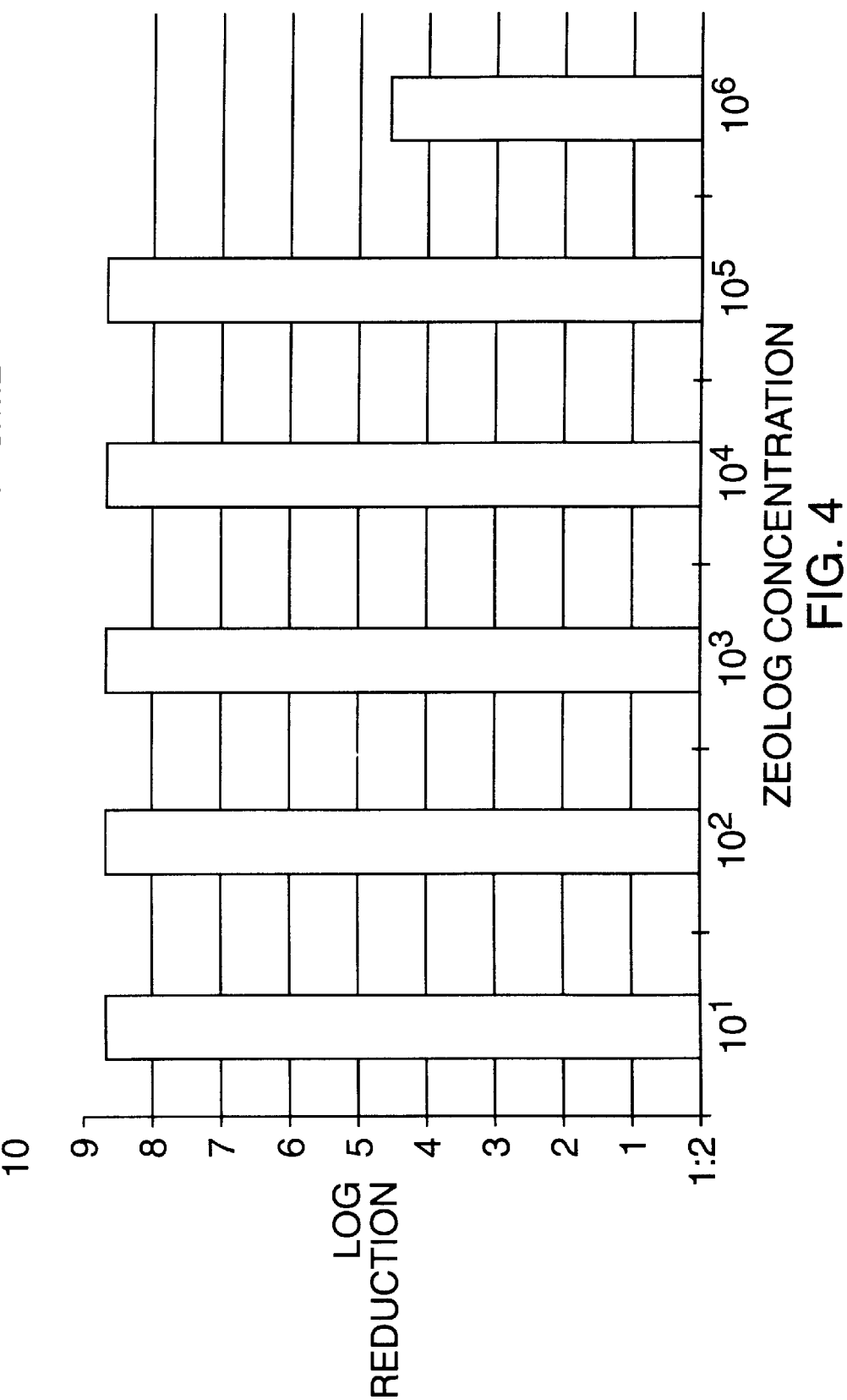
Figure 5:
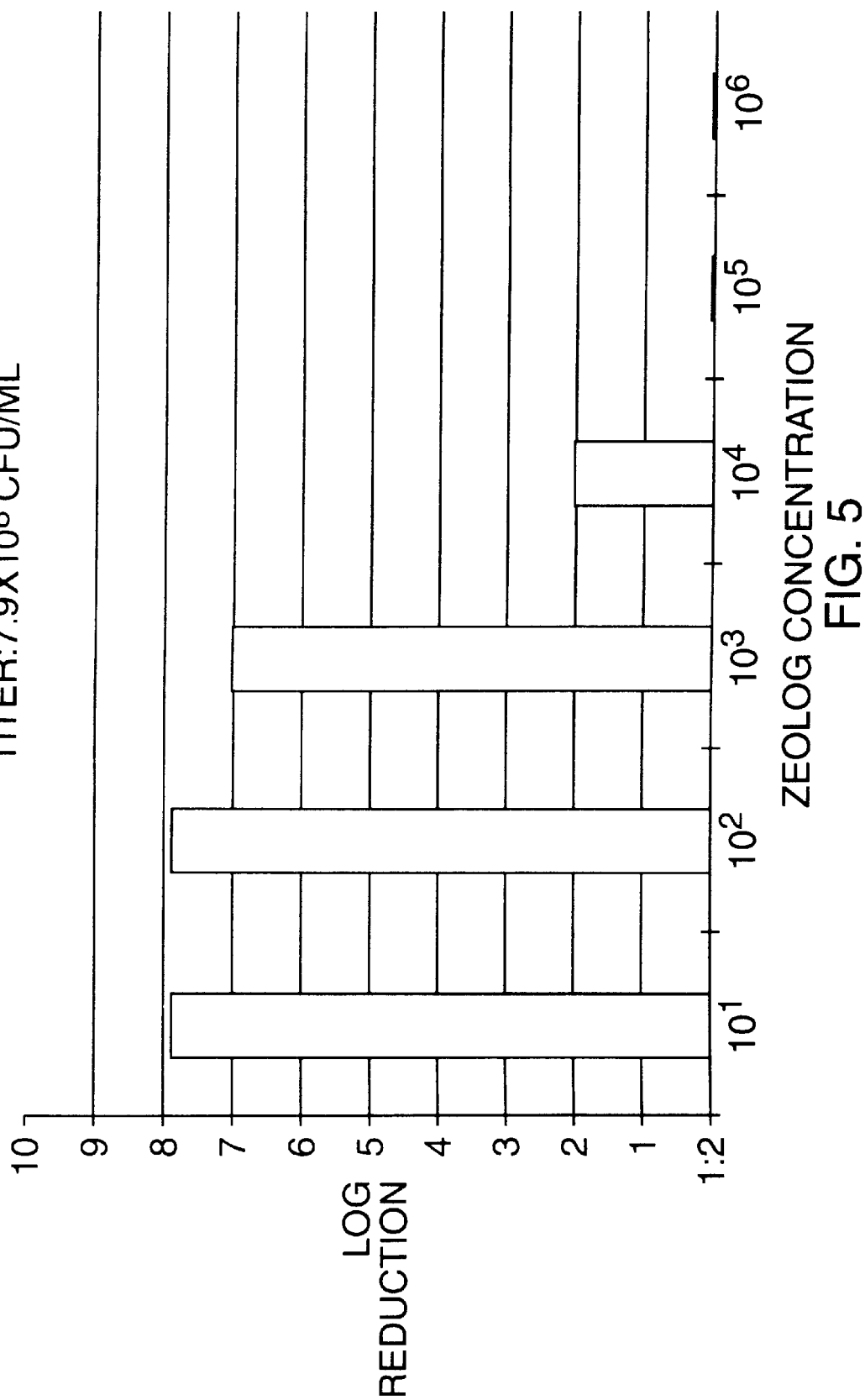
Figure 8:
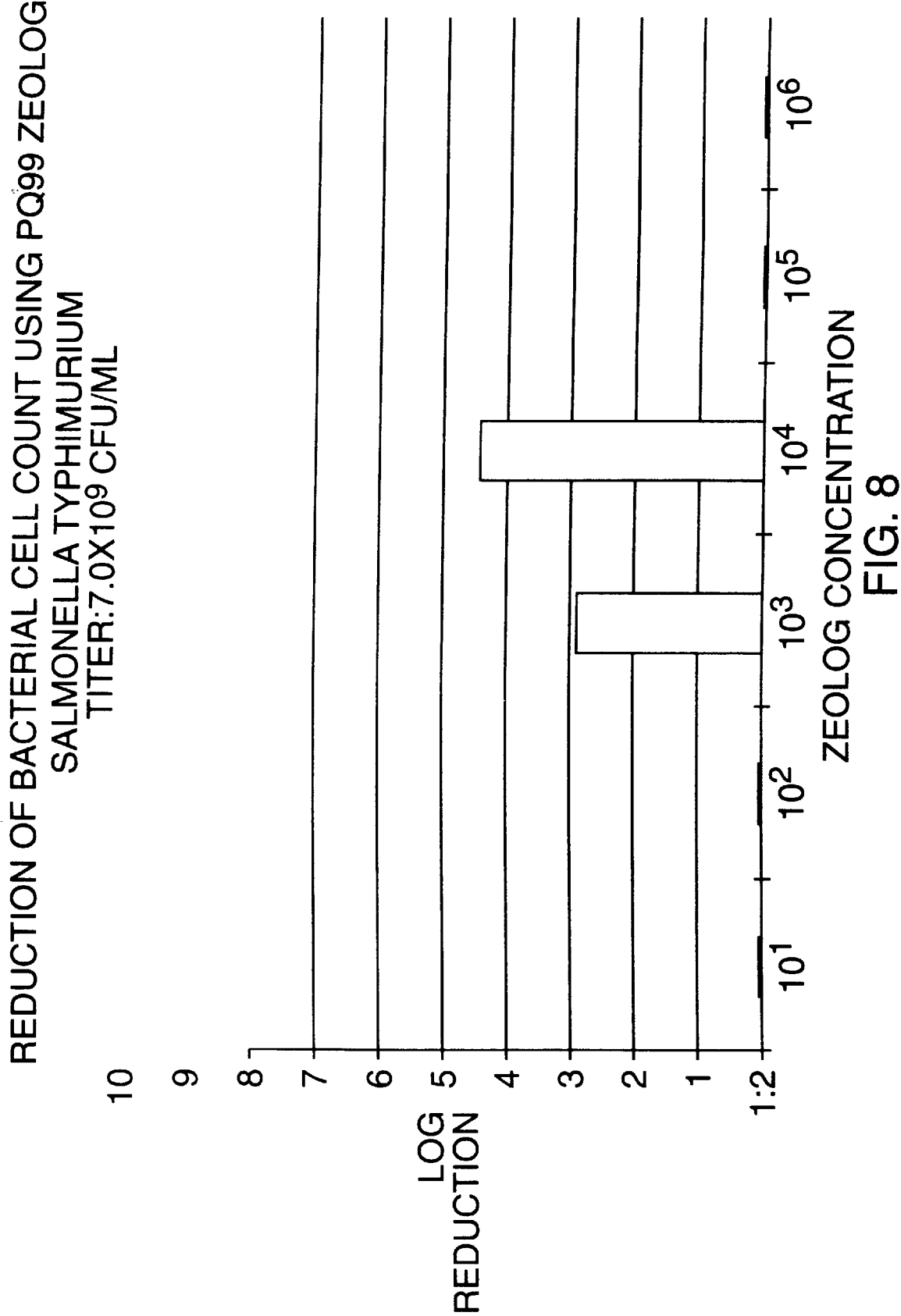
Figure 9:
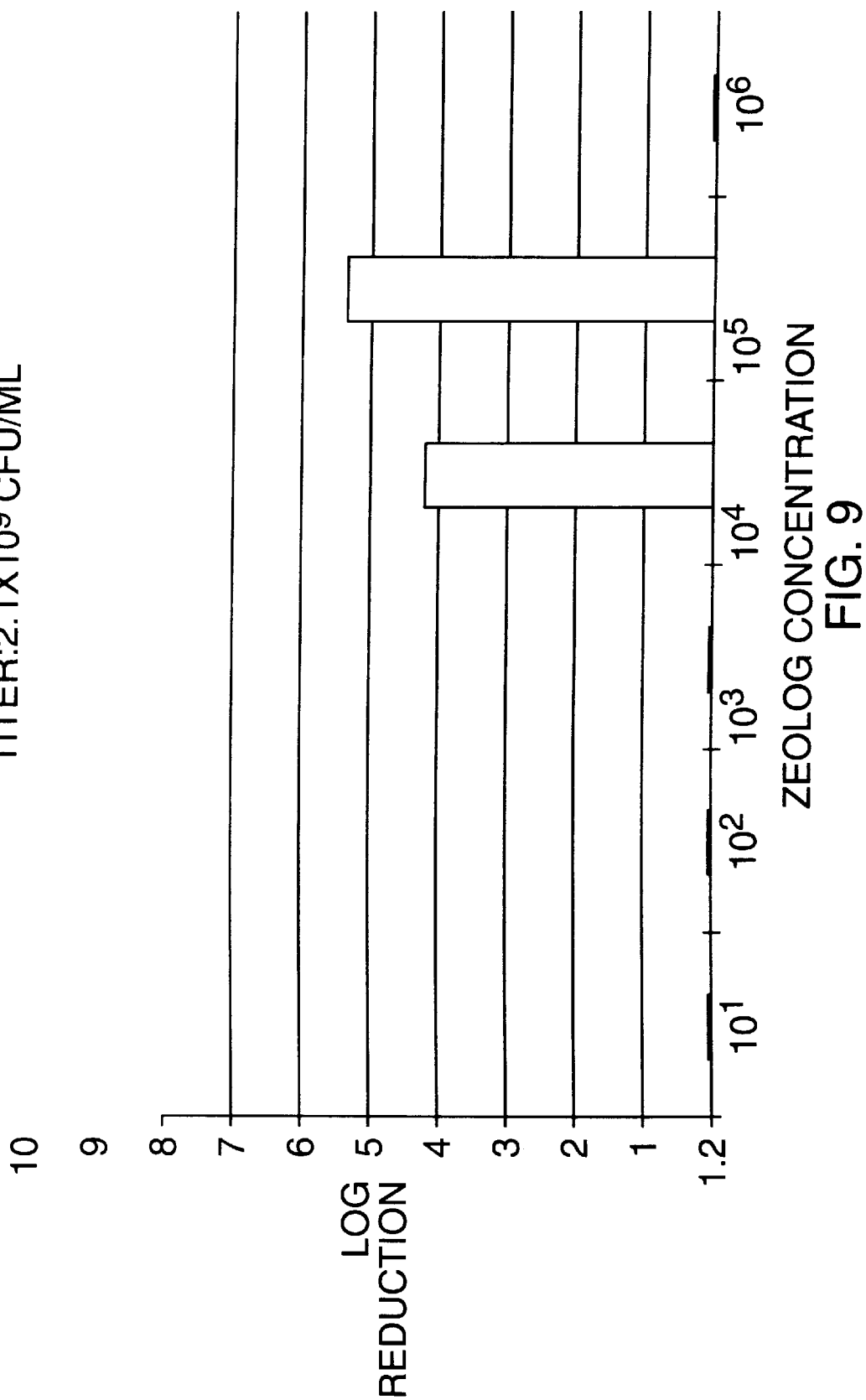

Zeolites are effective inhibitors of bacterial cell growth. For example, as illustrated in FIG. 4, the cell growth of Staphlococcus aureus was completely inhibited by a large range of concentrations of a clinoptilolite which has been derivatized with methanol (MeOH Zeolog, also known as ZeoLog-METH). In particular, the initial Staphlococcus aureus titer of $9.6 \times 10^8$ cfu/ml was reduced by $6 \times 10^8$ cfu/ml when using dilutions of this 45 mg/ml zeolite suspension which ranged between $10^{-1}$ and $10^{-5}$. Similarly, clinoptilolite derivatized with dichlorodimethylsilane completely inhibited Escherichia coli cell growth at $10^{-1}$ to $10^{-2}$ dilutions of a 45 mg/ml suspension of the derivatized clinoptilolite (see FIG. 5); and clinoptilolite derivatized with methyltriethoxy inhibited Salmonella typhimurium cell growth by up to $4 \times 10^5$ cfu/ml when a $10^{-4}$ dilution of the 45 mg/ml zeolite suspension was used (see FIG. 8). Hence, zeolites inhibit cell growth of all the types of bacteria which were tested.

Figure 6:
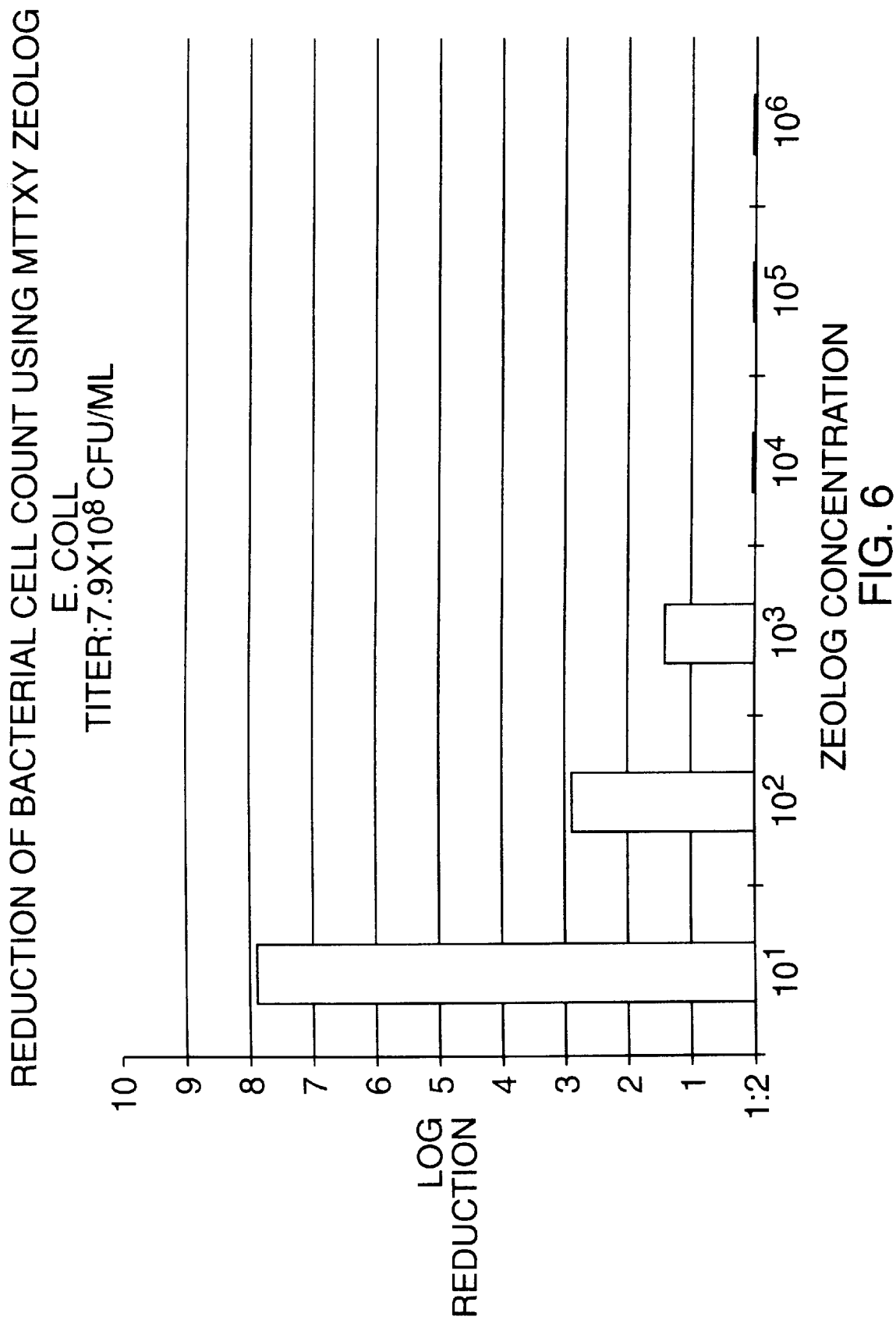
Figure 7:
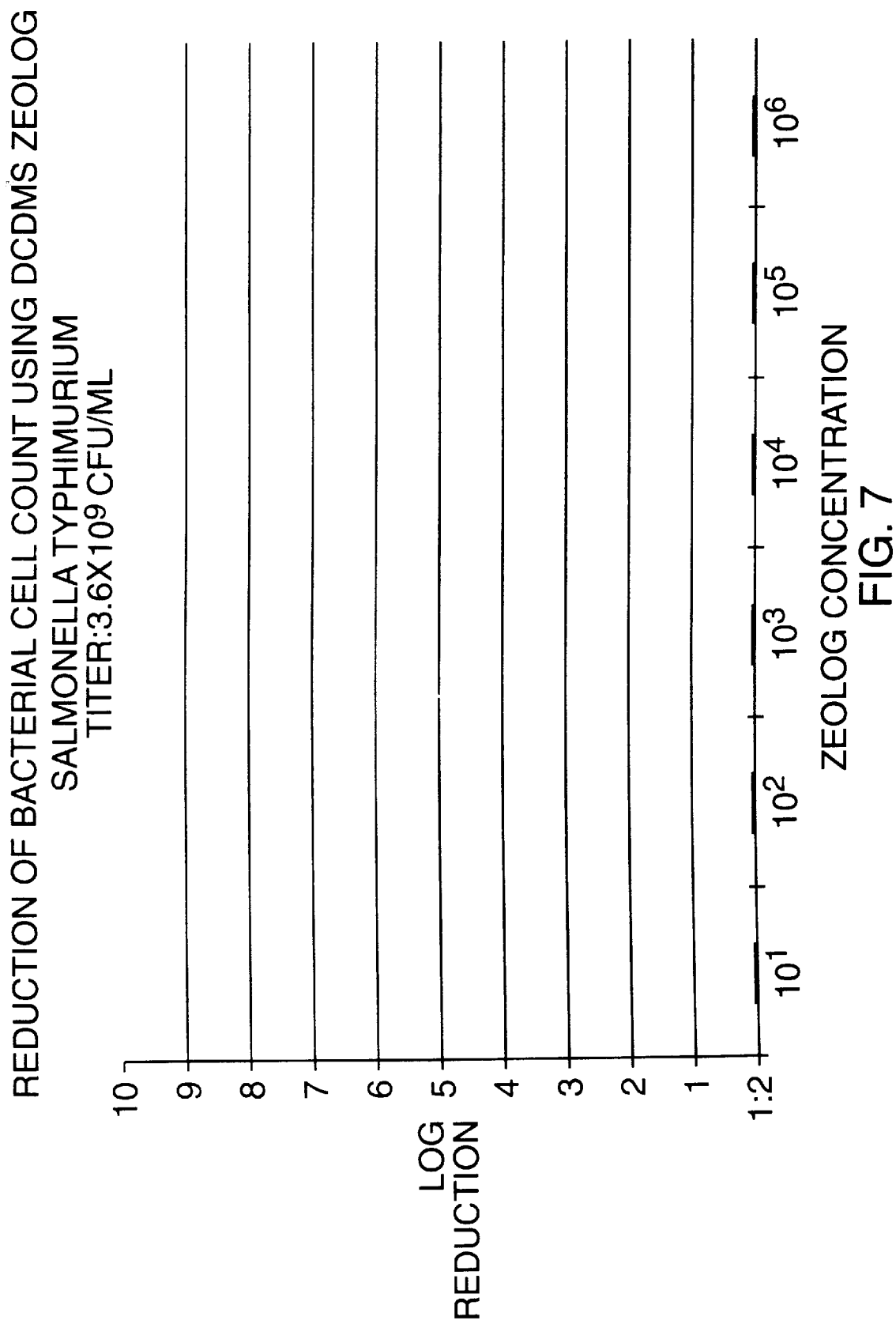

However, for one bacterial species, one type of zeolite derivative may be more effective at one concentration than another concentration. Thus, clinoptilolite which has been derivatized with methanol (MeOH Zeolog, also known as ZeoLog-Meth) was highly effective at wide range of concentrations against Staphlococcus aureus (see FIG. 4). But a dilution of $10^{-1}$ of a 45 mg/ml suspension of clinoptilolite derivatized with methyltriethoxy groups (ZeoLog-MeTE) was needed to cause strong inhibition of Staphlococcus aureus cell growth. Similarly, while a dichlorodimethylsilane derivative of clinoptilolite caused little inhibition of Salmonella typhimurium cell growth (see FIG. 7) in the range of concentrations which were tested, a methyltriethoxy derivative of clinoptilolite was an effective inhibitor of Salmonella typhimurium (see FIG. 8) at $10^{-3}$ and 10–4 dilutions (see FIG. 8). Similarly, a dichloro-dimethylsilane zeolite derivative was an effective inhibitor of Escherichia coli over a broad range of concentrations (see FIG. 5) while a methyltriethoxy derivative was strongly inhibitory only at $10^{-1}$ and 10–2 dilutions (FIG. 6). Thus, methanol derivatized zeolites are strong inhibitors of Staphlococcus aureus, while methyltriethoxy derivatized zeolites are effective against Salmonella typhimurium, and dichlorodimethylsilane zeolites are optimally effective against Escherichia coli.

EXAMPLE 4

Total Bacteriological Population in the Lungs of Chickens Fed Zeolites Derivatized with DCDMS Methods Batches of freshly hatched chicks were raised on feed containing clinoptilolite derivatized with DCDMS, in the amounts specified in Table II.

TABLE II

| Treatment[1] | Amount zeolite in feed |
| --- | --- |
| 1 | 50 mg/lb DCDMS zeolite |
| 2 | 250 mg/lb DCDMS zeolite |
| 3a | control: 125 mg/lb aluminated and nonderivatized zeolite |

TABLE II-continued

| Treatment[1] | Amount zeolite in feed |
| --- | --- |
| 3b | control: 125 mg/lb dealuminated but nonderivatized zeolite) |
| 4 | 500 mg/lb DCDMS zeolite |
| 5 | 125 mg/lb DCDMS zeolite |

This feed was the only feed given to these chickens from the time of hatching until slaughter, which occurred at about 7–8 weeks of age. The chickens were examined by a veterinarian for symptoms of disease, malnutrition and poor growth. The histopathology of the chickens, hearts, livers, spleens, kidneys, trachea and lungs were also observed (see Tables III and IV). While no overall toxic effects of this feeding regimen were observed, some lesions were observed in the trachea and lungs which were likely due to irritation or inhalation of foreign material (see Table IV). The number of colony forming units per gram of lung tissue was determined to ascertain whether one group of chickens had an increased propensity for lung infections, e.g. bacterial pneumonia.

Results

No negative effects upon the chickens were observed.

TABLE III HISTOPATHOLOGY REPORT: ZEOLITE EXPERIMENT #1

Heart—In most birds there were no alterations. A few had scattered and small infiltrations of lymphocytes between muscle bundles. Intimal proliferation in small arteries occurred in two birds.

Liver—The usual focal collections of lymphocytes were present in most of the livers. These foci were scattered in the parenchyma and in portal areas. In some birds the lymphocytes were mixed with immature granulocytes. The epithelium of occasional bile ducts was hypertrophic.

Spleen—No remarkable lesions.

Kidney—Focal collections of lymphocytes, in follicular formation or diffuse infiltration, were scattered in the cortex or medulla of several birds.

Trachea—An inflammation of varying severity involved the trachea of most birds. These lesions were characterized by infiltration of lymphocytes in the mucosa. The infiltrations were diffuse or follicular and involved focal are diffuse areas of the trachea. Little exudate was present in the lumen. The cilia were not involved.

Lung—Nodular collections of lymphocytes occurred in the mucosa of bronchi in all lungs. Granulomas, consisting of necrotic centers with surrounding lymphocytes, heterophiles and multinucleated giant cells, were present in the lumina of bronchi in many birds. Bacterial colonies were often present in the granulomas and mycelia were identified in two birds. Crystalline foreign material was observed in the lesions of one bird. Occasionally the infection had spread in the peribronchial tissue resulting in areas of pneumonia.

Foci of cartilage and/or bone were scattered in the parenchyma of many birds.

TABLE IV
SUMMARY OF LESIONS

| | Tracheitis* | | Lung* | | | |
| --- | --- | --- | --- | --- | --- | --- |
| | | Av. Score** | Granuloma | Bact | Fungus | Pneumonia |
| Tmt 1 | 12/24 | 0.51 | 5/24 | 1/24 | 1/24 | 0/24 |
| Tmt 2 | 20/24 | 1.50 | 12/23 | 4/23 | 0/23 | 10/23 |
| Tmt 3 | 18/24 | 1.25 | 10/24 | 5/24 | 0/24 | 6/24 |
| Tmt 4 | 12/24 | 0.83 | 9/24 | 1/24 | 1/24 | 0/24 |
| Tmt 5 | 17/24 | 0.95 | 6/24 | 4/24 | 0/24 | 6/24 |

*Number/Total
**Lesion Score (severity) 0 normal, 4 most severe.

There was no evidence of toxicity in these birds.

Only the lesions of the respiratory system were possibly related to the experiment. The lymphocytic infiltrations occurring in the liver, spleen and kidney are commonly observed in birds in the field. The occasional hyperplasia of the bile duct epithelium was not associated with the experimental treatment. Peri-ductal infiltrations of heterophiles are observed occasionally in field birds.

The lesions of the trachea and lung were those of irritation and/or inhalation of unidentified foreign material. Tracheitis was possibly the result of ammonia levels. The location of the granulomas in the lumina of bronchi suggested the lesions were related to inhalation. The lesions appeared to arise from some material or organism which had lodged on the mucosal surface. Infection in some cases had spread to adjacent areas of the lung.

Chickens were tested to determine whether feeding derivatized zeolites increased or decreased bacterial infections in the lung. The treatment regimen was provided in Table II. Table V summarizes the results.

TABLE V
Effect of Feeding Chickens Clinoptilolite derivatized with DCDMS

| TREATMENT[1] | REPL[2] | LUNG CFU/MAC[3] |
| --- | --- | --- |
| 1–50 mg/lb | 1 | 3000/gm |
| 1–50 mg/lb | 2 | 12000/gm |
| 2–250 mg/lb | 1 | 450/gm |
| 2–250 mg/lb | 2 | 800/gm |
| 3a-control[4] | 1 | 60000/gm |
| 3b-control[5] | 2 | 15000/gm |
| 4–500 mg/lb | 1 | 115/gm |
| 4–500 mg/lb | 2 | 180/gm |
| 5–125 mg/lb | 1 | 1500/gm |
| 5–125 mg/lb | 2 | 12000/gm |

[1]Amount DCDMS-derivatized clinoptilolite in feed.
[2]Replicate number.
[3]Number of colony forming units observed on a MacConkey agar plates per gram of lung tissue.
[4]3a Control - chickens were fed 125 mg/lb aluminated and nonderivatized zeolite.
[5]3b Control - chickens were fed 125 mg/lb dealuminated and nonderivatized zeolite.

As illustrated in Table V, feeding increasing amounts of dealuminated, derivatized zeolite to chickens decreases the number of colony forming units (CFU) in the lung. Chickens fed aluminated zeolites had 60,000 CFU per gram lung tissue. Chickens fed dealuminated zeolites had five-fold fewer CFU. Hence, dealumination of zeolites fed to chickens causes a reduction in bacterial infection, even when the zeolites are not derivatized.

Derivatization provides even greater anti-bacterial effect. Hence, the CFU per gram of lung tissue decreases by at least about twenty-fold, from 3000–12000 when chickens are fed 50 mg derivatized zeolite per pound of feed, to 115–180 when chickens are fed 500 mg derivatized zeolite per pound of feed. Feeding derivatized zeolite therefore protected chickens against lung infection.

What is claimed:

1. A method for preventing a microorganism from growing on a surface or in an absorbent material which method comprises: incorporating an effective amount of dealuminated tectosilicate onto said surface or into said absorbent material to inhibit said microorganism from growing.

2. The method of claim 1 wherein said dealuminated tectosilicate is dealuminated analcite, brewsterite, habazite, clinoptilolite, dachiardite, erionite, faujasite, ferrierite, flakite, gmelinite, harmotone, heulandite, leucite, levynite, mesolite, mordenite, natrolite, nepheline, noselite, paulingite, phillipsite, ptilolite, scolecite, stilbite, or yugawaralite.

3. The method of claim 1 wherein said dealuminated tectosilicate is dealuminated clinoptilolite.

4. The method of claim 1 wherein said zeolite is hydrophobic microporous crystalline tectosilicate of regular geometry having aluminum-free sites in a silaceous lattice;
wherein said sites have about 1 to about 4 associated moieties of the formula $\equiv$SiOR; and
wherein each R is a substituent that is a weaker point electric source than aluminum.

5. The method of claim 4 wherein each R is a substituent that is a weaker point electric source than hydroxy.

6. The method of claim 4 wherein each R is selected from the group consisting of $C_1$–$C_4$ alkyl, $C_1$–$C_4$ alkoxy, $C_1$–$C_4$ acyl, and $SiR'_n X_p$, wherein:
each R' is selected from the group consisting of $C_1$–$C_4$ alkyl, cyclolalkyl, aryl, $C_1$–$C_4$ acyl, and aralkyl;
each X is a halogen or a $C_1$–$C_4$ alkoxy;
each n is an integer of 0 to 3; and
each p is 3–n.

7. The method of claim 4 wherein a aluminum-free site is bridged by 1 or 2 $SiR'_q$, wherein
each R' is selected from the group consisting of $C_1$–$C_4$ alkyl, cyclolalkyl, aryl, $C_1$–$C_4$ acyl, and aralkyl.

8. The method of claim 1 wherein said dealuminated tectosilicate is a dealuminated dichlorodimethyl silane zeolite, ZeoLog-MeTE, ZeoPhob™, ZeoLog™, ZeoLogCN-METHANOL™, Zeolite A, Zeolite B, Zeolite D, Zeolite E, Zeolite F, Zeolite H, Zeolite J, Zeolite KG, Zeolite L, Zeolite M, Zeolite O, Zeolite Q, Zeolite R, Zeolite S, Zeolite T, Zeolite W, Zeolite X, Zeolite Y, and Zeolite Z.

9. The method of claim 1 wherein said surface is skin, wall, floor, countertop, or wallcovering.

10. The method of claim 1 wherein said absorbent material is a diaper, clothing, bedding, bedpad, surgical apparel, or surgical mask.

11. The method of claim 1 wherein said effective amount of dealuminated tectosilicate is about 1% to about 50% of the weight of the absorbent material.

12. The method of claim 1 wherein said effective amount of dealuminated tectosilicate is about 15% to about 25% of the weight of the absorbent material.

13. The method of claim 1 wherein said microorganism is a gram negative species of bacteria.

14. The method of claim 13 wherein said gram negative species is an Enterobacteriaceae.

15. The method of claim 14 wherein said Enterobacteriaceae is a Proteus.

16. The method of claim 15 wherein said Proteus is *Proteus mirabilis, Proteus vulgaris, Proteus penneri* or *Proteus myxofaciens.*

17. The method of claim 14 wherein said Enterobacteriaceae is a Klebsiella, Providencia, Yersinia, Erwinia, Enterobacter, Salmonella, Serratia, Aerobacter and Escherichia.

18. The method of claim 1 wherein said microorganism is *Escherichia coli* or *Staphylococcus aureous.*

19. The method of claim 14 wherein said gram negative bacteria is Pseudomonas, Shegella, Vibrio, Aeromonas, or Campylobacter.

20. The method of claim 1 wherein said microorganism is a gram positive microorganism.

21. The method of claim 20 wherein said microorganism is Streptococcus, Staphylococcus, Lactobacillus, Micrococcus or Moraxella-Neisseria.

22. A method for preventing a microorganism from growing on a surface or in an absorbent material which method comprises: incorporating an effective amount of a dealuminated tectosilicate onto said surface or into said absorbent material to inhibit said microorganism from growing, wherein said dealuminated tectosilicate is substituted with at least one substituent having a weaker point electric source than aluminum.

* * * * *